US010208344B2

(12) United States Patent
Gurney-Smith et al.

(10) Patent No.: US 10,208,344 B2
(45) Date of Patent: Feb. 19, 2019

(54) METHODS AND PROBES FOR MONITORING MARINE WATER

(71) Applicants: Helen Gurney-Smith, Nanaimo (CA); Catherine Thomson, Nanaimo (CA); Stewart Johnson, Nanaimo (CA)

(72) Inventors: Helen Gurney-Smith, Nanaimo (CA); Catherine Thomson, Nanaimo (CA); Stewart Johnson, Nanaimo (CA)

(*) Notice: Subject to any disclaimer, the term of this patent is extended or adjusted under 35 U.S.C. 154(b) by 178 days.

(21) Appl. No.: 14/909,075

(22) PCT Filed: Jul. 28, 2014

(86) PCT No.: PCT/IB2014/063481
§ 371 (c)(1),
(2) Date: Jan. 29, 2016

(87) PCT Pub. No.: WO2015/015400
PCT Pub. Date: Feb. 5, 2015

(65) Prior Publication Data
US 2016/0201127 A1 Jul. 14, 2016

Related U.S. Application Data

(60) Provisional application No. 61/861,842, filed on Aug. 2, 2013.

(51) Int. Cl.
*C12Q 1/6876* (2018.01)
*C07H 21/04* (2006.01)
*C12Q 1/6895* (2018.01)

(52) U.S. Cl.
CPC .......... *C12Q 1/6876* (2013.01); *C07H 21/04* (2013.01); *C12Q 1/6895* (2013.01); *C12Q 2600/156* (2013.01); *C12Q 2600/158* (2013.01); *C12Q 2600/16* (2013.01)

(58) Field of Classification Search
CPC ............................. C12Q 1/68; C12Q 2600/156
See application file for complete search history.

(56) References Cited

PUBLICATIONS

Gurney-Smith, H. et al. Journal of Shellfish Research 31(1):292-293 (Mar./Apr. 2012).*
Dondero, F. et al. Aquatic Toxicology 78S:S13 (2006).*
Domeneghetti et al.: "How gene expression profiles disclose vital processes and immune responses in *Mytilus* spp.", Invertebrate Survival Journal, 2011, pp. 179-189, vol. 8.
Li et al., 2010 "Expression of Mytilus immune genes in response to experimental challenges varied according to the site of collection." Fish & Shellfish Immunology 28(4): 640-648.
(Continued)

*Primary Examiner* — Diana B Johannsen
(74) *Attorney, Agent, or Firm* — Baumgartner Patent Law; Marc Baumgartner

(57) ABSTRACT

A method of biomonitoring marine water is provided, as are probes and kits. The method comprises: extracting messenger Ribonucleic Acid (mRNA) from *Mytilus* species; preparing cDNA from the mRNA; hybridizing a plurality of probes with the cDNA to provide a set of hybridized cDNA, the probes consisting of at least 20 consecutive nucleotides of at least 50 sequences of SEQ ID NO: 1-122; and quantifying an abundance of the set of hybridized cDNA, thereby biomonitoring marine water.

5 Claims, 2 Drawing Sheets
Specification includes a Sequence Listing.

(56) References Cited

PUBLICATIONS

Veldhoen et al., 2011 "Relationship between mRNA biomarker candidates and location near a marine municipal wastewater outfall in the benthic indicator species *Modiolus modiolus* (L.)." Aquatic Toxicology 105(1-2): 119-126.

Veldhoen et al., 2009 "Gene expression profiling in the deep water horse mussel *Modiolus modiolus* (L.) located near a marine municipal wastewater outfall." Aquatic Toxicology 93(2-3): 116-124 from Modiolus modiolus.

WIPO, Canadian International Searching Authority, Written Opinion of the International Searching Authority dated Dec. 8, 2014, International Patent Application No. PCT/IB2014/063481, 8 Pages.

WIPO, Canadian International Searching Authority, International Search Report dated Dec. 8, 2014, International Patent Application No. PCT/IB2014/063481, 6 Pages.

\* cited by examiner

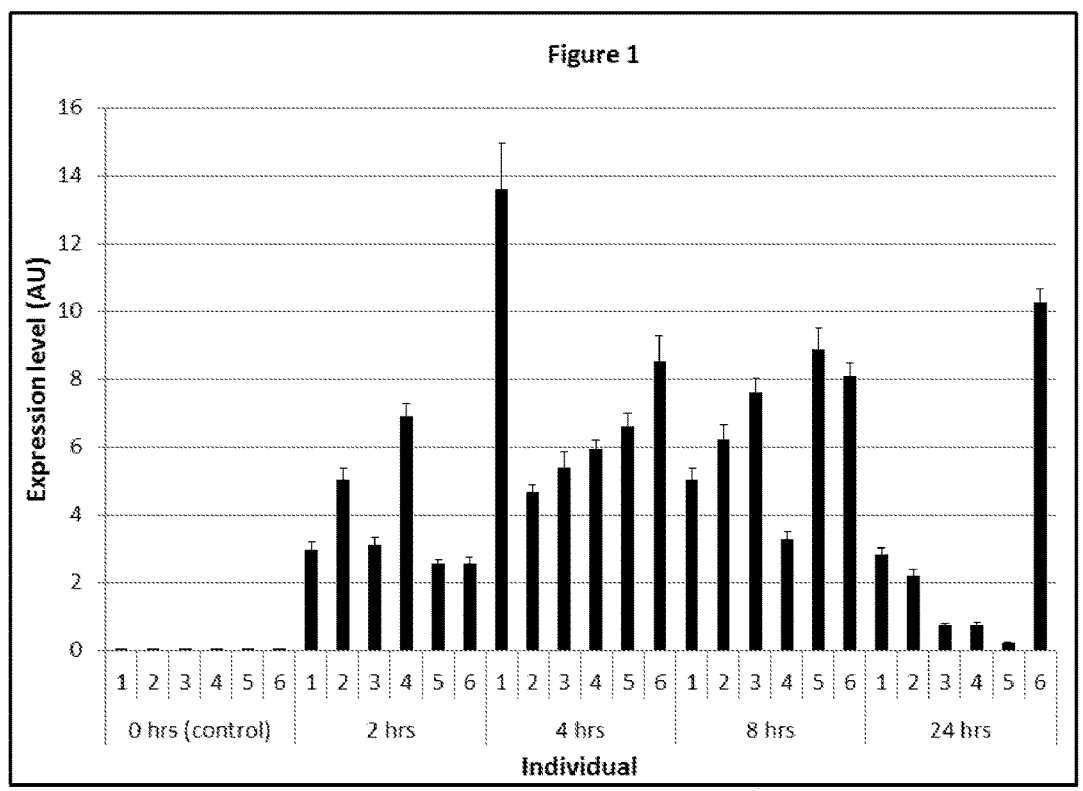

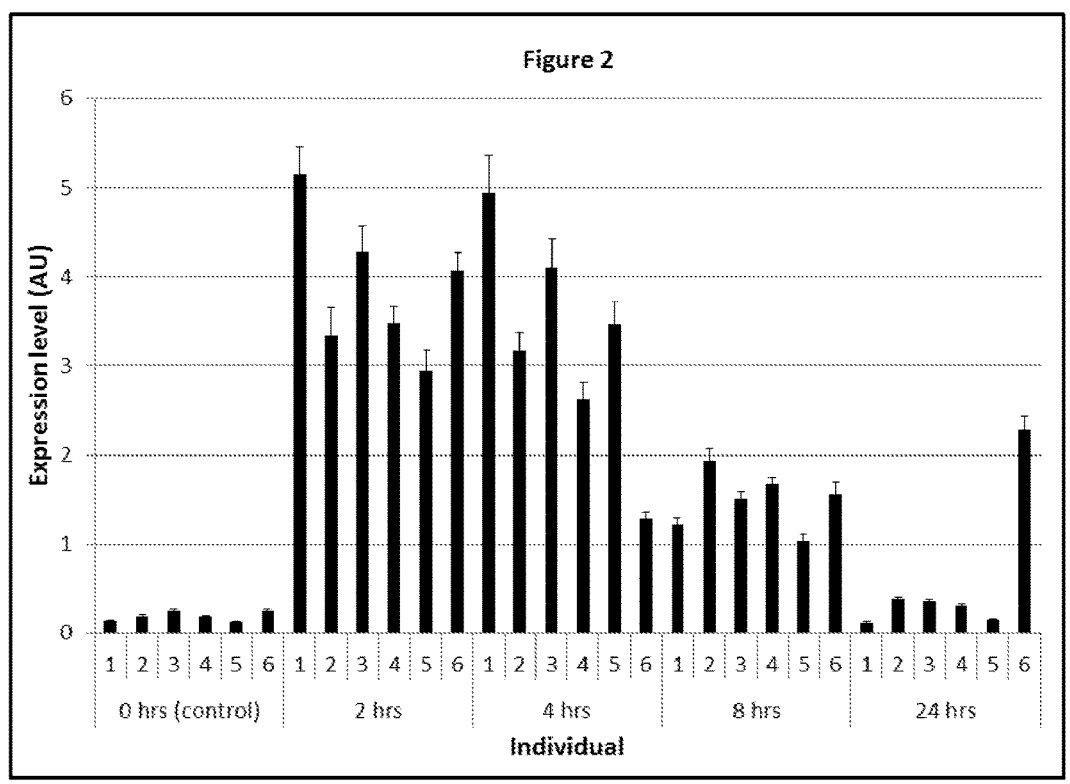

SEQUENCE LISTING

<160> NUMBER OF SEQ ID NOS: 122

<210> SEQ ID NO 1
<211> LENGTH: 60
<212> TYPE: DNA
<213> ORGANISM: Mytilus edulis

<400> SEQUENCE: 1
cccattgctc aatgcccagg ttgtttatag ggcattaatt gtgtaaataa ctaatagata     60

<210> SEQ ID NO 2
<211> LENGTH: 60
<212> TYPE: DNA
<213> ORGANISM: Mytilus edulis

```
<400> SEQUENCE: 2
ggaagtcaca tcttgtatga ttctactaca gataatgtat caagtccagg aatgtatgtt      60

<210> SEQ ID NO 3
<211> LENGTH: 60
<212> TYPE: DNA
<213> ORGANISM: Mytilus edulis

<400> SEQUENCE: 3
gtacctgcat actttaatga ttctcaaaga ctagccacaa aggatgctgg tttcattgca      60

<210> SEQ ID NO 4
<211> LENGTH: 60
<212> TYPE: DNA
<213> ORGANISM: Mytilus edulis

<400> SEQUENCE: 4
cataatgaag atggttctaa aggaatgaat caagacgact caaaagggtt caatcaagac      60

<210> SEQ ID NO 5
<211> LENGTH: 60
<212> TYPE: DNA
<213> ORGANISM: Mytilus edulis

<400> SEQUENCE: 5
gactctttca ctgtggtaat agtggtttta tgatgtcttg gagtttaaac tgttaagaac      60

<210> SEQ ID NO 6
<211> LENGTH: 60
<212> TYPE: DNA
<213> ORGANISM: Mytilus edulis

<400> SEQUENCE: 6
gaggtatgca cttggaaaat gaaaaatgca tctgcgtgaa attgctcata ctatttgcaa      60

<210> SEQ ID NO 7
<211> LENGTH: 60
<212> TYPE: DNA
<213> ORGANISM: Mytilus edulis

<400> SEQUENCE: 7
gtaccatcgc gtaggtttca aagtcctact gatgaaatta caaaagttaa aagactagaa      60

<210> SEQ ID NO 8
<211> LENGTH: 60
<212> TYPE: DNA
<213> ORGANISM: Mytilus edulis

<400> SEQUENCE: 8
tgattcaagg cagagctaaa ggagttgaag agacaaagga gcgagtcatt aatattgaac      60

<210> SEQ ID NO 9
<211> LENGTH: 60
<212> TYPE: DNA
<213> ORGANISM: Mytilus edulis

<400> SEQUENCE: 9
caagtatttt gaaaagggta ttccaaccac tggacacact gaaatgttaa catgattgaa      60

<210> SEQ ID NO 10
<211> LENGTH: 60
<212> TYPE: DNA
<213> ORGANISM: Mytilus galloprovincialis
```

<400> SEQUENCE: 10
ataatgaaac tgggaggtcg gctgatgttc accttgattt acttaaacat tgaaacaagc    60

<210> SEQ ID NO 11
<211> LENGTH: 60
<212> TYPE: DNA
<213> ORGANISM: Mytilus edulis

<400> SEQUENCE: 11
ggattaaaat gggtggttgt tcccaaaaaa tccctcattt cttttttctc catgattaac    60

<210> SEQ ID NO 12
<211> LENGTH: 60
<212> TYPE: DNA
<213> ORGANISM: Mytilus edulis

<400> SEQUENCE: 12
gtgagtaggg tcattttcgt ggaaacaggt cttcttaatt tgatgacata atgtatgtta    60

<210> SEQ ID NO 13
<211> LENGTH: 60
<212> TYPE: DNA
<213> ORGANISM: Mytilus edulis

<400> SEQUENCE: 13
cacccacata ttagtattgg aagaaaaaac ctgccaaata ttgagttgat ctctaatcca    60

<210> SEQ ID NO 14
<211> LENGTH: 60
<212> TYPE: DNA
<213> ORGANISM: Mytilus edulis

<400> SEQUENCE: 14
cgcatttata acatacatca ttccactcga agaaataaac tttcccccaa tctagtcaat    60

<210> SEQ ID NO 15
<211> LENGTH: 60
<212> TYPE: DNA
<213> ORGANISM: Mytilus edulis

<400> SEQUENCE: 15
gaggagatcc cttccgagat tttgagtaaa atgacagttt taattgagtt ccaattaaca    60

<210> SEQ ID NO 16
<211> LENGTH: 60
<212> TYPE: DNA
<213> ORGANISM: Mytilus edulis

<400> SEQUENCE: 16
gcaatgccaa aataagatgc gattttaatt attgcaatga actttctttc agaccactgc    60

<210> SEQ ID NO 17
<211> LENGTH: 60
<212> TYPE: DNA
<213> ORGANISM: Mytilus edulis

<400> SEQUENCE: 17
cagacaagag attactggac tttccagttc cattcagtat tattgattcc gtccaagaaa    60

<210> SEQ ID NO 18
<211> LENGTH: 60
<212> TYPE: DNA
<213> ORGANISM: Mytilus edulis

```
<400> SEQUENCE: 18
tgcagaatgt gtaacctaaa gggaaggatt ctaaaacaga tcaaacgaca tctggaggaa      60

<210> SEQ ID NO 19
<211> LENGTH: 60
<212> TYPE: DNA
<213> ORGANISM: Mytilus edulis

<400> SEQUENCE: 19
cttgggattg taacctttgg attggaaagt gaagattgat caaagcaaag gacttaaatt      60

<210> SEQ ID NO 20
<211> LENGTH: 60
<212> TYPE: DNA
<213> ORGANISM: Mytilus galloprovincialis

<400> SEQUENCE: 20
gctatctctt tgatcttctg agtgctgtga ttaagtaaca tttccatgta tgctttactt      60

<210> SEQ ID NO 21
<211> LENGTH: 60
<212> TYPE: DNA
<213> ORGANISM: Mytilus galloprovincialis

<400> SEQUENCE: 21
aacgtcagga caaatacaag cattaaatca atatacacat gtgaacgtca ggacaaaact      60

<210> SEQ ID NO 22
<211> LENGTH: 60
<212> TYPE: DNA
<213> ORGANISM: Mytilus galloprovincialis

<400> SEQUENCE: 22
gctagtgtcg tttgtgatag tgaatgtcct tgtggaaata caaaacggcc ttgtatatgt      60

<210> SEQ ID NO 23
<211> LENGTH: 60
<212> TYPE: DNA
<213> ORGANISM: Mytilus galloprovincialis

<400> SEQUENCE: 23
cagggattct tggcattatt ttcaggtgac actggtgaaa ttaaaagtga agtaagagaa      60

<210> SEQ ID NO 24
<211> LENGTH: 60
<212> TYPE: DNA
<213> ORGANISM: Mytilus edulis

<400> SEQUENCE: 24
gacgtctgaa aagcagtaga cctgtttttt actcgcataa tttgcatctt atgtagaatt      60

<210> SEQ ID NO 25
<211> LENGTH: 60
<212> TYPE: DNA
<213> ORGANISM: Mytilus edulis

<400> SEQUENCE: 25
cttgtgtgat ttcatgttac caagaacaat gattagttgg tagagatagc atcagtagag      60

<210> SEQ ID NO 26
<211> LENGTH: 60
<212> TYPE: DNA
<213> ORGANISM: Mytilus edulis
```

<400> SEQUENCE: 26
gccttatcgt ctgaataatt aaatggcgac tctcagctgt aattgttgtt aaaatatgca    60

<210> SEQ ID NO 27
<211> LENGTH: 60
<212> TYPE: DNA
<213> ORGANISM: Mytilus edulis

<400> SEQUENCE: 27
ctccgccaga ggctggcaaa aagttttata ttgacaaagg aagctcaaaa tcaataaaat    60

<210> SEQ ID NO 28
<211> LENGTH: 60
<212> TYPE: DNA
<213> ORGANISM: Mytilus edulis

<400> SEQUENCE: 28
gtgtattgat aaagcatgaa atgagagcaa agaaaaatag gcggcatttt acttgtaact    60

<210> SEQ ID NO 29
<211> LENGTH: 60
<212> TYPE: DNA
<213> ORGANISM: Mytilus edulis

<400> SEQUENCE: 29
gtatgaacat ctgctacaac agattccata acatatgaat cttcagacat taagaacgac    60

<210> SEQ ID NO 30
<211> LENGTH: 60
<212> TYPE: DNA
<213> ORGANISM: Mytilus edulis

<400> SEQUENCE: 30
ctggtatcca gcctgtttgt ggcaaataaa acaaggttgt aaaaaagatt atggatttgt    60

<210> SEQ ID NO 31
<211> LENGTH: 60
<212> TYPE: DNA
<213> ORGANISM: Mytilus galloprovincialis

<400> SEQUENCE: 31
gggctatcga agagatgggg aaaactcaag atacggatga aaagcaccat taaaagatat    60

<210> SEQ ID NO 32
<211> LENGTH: 60
<212> TYPE: DNA
<213> ORGANISM: Mytilus galloprovincialis

<400> SEQUENCE: 32
gccttaatgt ttcctgggtg atgcttacac atttgaattg caattgtacc gttcatgtac    60

<210> SEQ ID NO 33
<211> LENGTH: 60
<212> TYPE: DNA
<213> ORGANISM: Mytilus galloprovincialis

<400> SEQUENCE: 33
ccaaaaagga ggcaactcaa atgttaggac agataataga atgtgttagg aatttaccta    60

<210> SEQ ID NO 34
<211> LENGTH: 60
<212> TYPE: DNA
<213> ORGANISM: Mytilus galloprovincialis

```
<400> SEQUENCE: 34
ttattgaatt atttctgttg ccgttacgtc tgtttatcca cgagtctttt aggaatctct      60

<210> SEQ ID NO 35
<211> LENGTH: 60
<212> TYPE: DNA
<213> ORGANISM: Mytilus edulis

<400> SEQUENCE: 35
gaagcagaca gatctattca tgatgccctg tgtgttctta ctcagacagt caaggaaacc      60

<210> SEQ ID NO 36
<211> LENGTH: 60
<212> TYPE: DNA
<213> ORGANISM: Mytilus galloprovincialis

<400> SEQUENCE: 36
agagttacat aacttggaaa aaagagttga ctcaatgttg tgatctgatc tcagggataa      60

<210> SEQ ID NO 37
<211> LENGTH: 60
<212> TYPE: DNA
<213> ORGANISM: Mytilus edulis

<400> SEQUENCE: 37
gtgcaaagtt atgactgatt gtttgcgatc aaatcgctat cgtggtgata ataaattgtg      60

<210> SEQ ID NO 38
<211> LENGTH: 60
<212> TYPE: DNA
<213> ORGANISM: Mytilus edulis

<400> SEQUENCE: 38
cgacagaacc aaggatttaa tcagtgtccg cagttaaatt gaatatgtag tctttgttgc      60

<210> SEQ ID NO 39
<211> LENGTH: 60
<212> TYPE: DNA
<213> ORGANISM: Mytilus edulis

<400> SEQUENCE: 39
ggtgtcaaag atcaccaata ttccacattt tctgtttgac agtaaccatc ataaatacac      60

<210> SEQ ID NO 40
<211> LENGTH: 60
<212> TYPE: DNA
<213> ORGANISM: Mytilus edulis

<400> SEQUENCE: 40
gcattagatt tgacaaatga attgttaaca ttagtcccag gtcatgacag ggctttaaat      60

<210> SEQ ID NO 41
<211> LENGTH: 60
<212> TYPE: DNA
<213> ORGANISM: Mytilus edulis

<400> SEQUENCE: 41
acgtgattgc cgattgcggt aaattattgc ctgtgaattt atgatgtgaa cattttagat      60

<210> SEQ ID NO 42
<211> LENGTH: 60
<212> TYPE: DNA
<213> ORGANISM: Mytilus edulis
```

<400> SEQUENCE: 42
gtatcctcat ttctgttggt gatcgttatt ttcgattttg ttgttgacat gagacaatct    60

<210> SEQ ID NO 43
<211> LENGTH: 60
<212> TYPE: DNA
<213> ORGANISM: Mytilus edulis

<400> SEQUENCE: 43
gggcagattt agaatataaa cctcctgtag aaaaatcttg acacaaggat gactagttta    60

<210> SEQ ID NO 44
<211> LENGTH: 60
<212> TYPE: DNA
<213> ORGANISM: Mytilus edulis

<400> SEQUENCE: 44
agtgattaca cattcagtca gaaatccttg tcaagttgtt attgccagtt atacttgcat    60

<210> SEQ ID NO 45
<211> LENGTH: 60
<212> TYPE: DNA
<213> ORGANISM: Mytilus edulis

<400> SEQUENCE: 45
atgatgatta tgctgggtat caagaccatg actttggagg tgctagtggg ttctcctttg    60

<210> SEQ ID NO 46
<211> LENGTH: 60
<212> TYPE: DNA
<213> ORGANISM: Mytilus edulis

<400> SEQUENCE: 46
agagcattta aagagagaaa taaaatgggt cggtttgctg aaacagatcc tgaagaactg    60

<210> SEQ ID NO 47
<211> LENGTH: 60
<212> TYPE: DNA
<213> ORGANISM: Mytilus edulis

<400> SEQUENCE: 47
taggtcatgg acttggagcc ggtggtcatt tacctggcct tagtaaagat attgaaaaaa    60

<210> SEQ ID NO 48
<211> LENGTH: 60
<212> TYPE: DNA
<213> ORGANISM: Mytilus edulis

<400> SEQUENCE: 48
ggattttggc ttttttatta gaatagttag catgtgctgt aaaatcccta tcagatgtcc    60

<210> SEQ ID NO 49
<211> LENGTH: 60
<212> TYPE: DNA
<213> ORGANISM: Mytilus edulis

<400> SEQUENCE: 49
gcaaaaccat gccgataggt tgtgtagaaa aataaatttt tgctcagttt tgctgatgaa    60

<210> SEQ ID NO 50
<211> LENGTH: 60
<212> TYPE: DNA
<213> ORGANISM: Mytilus edulis

```
<400> SEQUENCE: 50
gacatccaat atgataaata tgttgtactt gtgtaagact ccaataacca ggggagataa        60

<210> SEQ ID NO 51
<211> LENGTH: 60
<212> TYPE: DNA
<213> ORGANISM: Mytilus edulis

<400> SEQUENCE: 51
attaaaggca gaaaagttag agcttctgaa ccagatgaaa cagttgtacc tcggccgcga        60

<210> SEQ ID NO 52
<211> LENGTH: 60
<212> TYPE: DNA
<213> ORGANISM: Mytilus galloprovincialis

<400> SEQUENCE: 52
ccggacgggt ttgattacgt tgcggctggt gatatccaag cattttcatt atataaaaaa        60

<210> SEQ ID NO 53
<211> LENGTH: 60
<212> TYPE: DNA
<213> ORGANISM: Mytilus galloprovincialis

<400> SEQUENCE: 53
ctgtcattgt tttacatcac ttgcatgtga gtatatggta attaactgaa taggttggag        60

<210> SEQ ID NO 54
<211> LENGTH: 60
<212> TYPE: DNA
<213> ORGANISM: Mytilus edulis

<400> SEQUENCE: 54
gtaattatga ccaatcattt gtaatccatc ctggcaaaag actaccatgc ttttatctga        60

<210> SEQ ID NO 55
<211> LENGTH: 60
<212> TYPE: DNA
<213> ORGANISM: Mytilus edulis

<400> SEQUENCE: 55
catataattt attgatataa ctaagagtgt tattgatcat gcatgagggt ctggatgggg        60

<210> SEQ ID NO 56
<211> LENGTH: 60
<212> TYPE: DNA
<213> ORGANISM: Mytilus edulis

<400> SEQUENCE: 56
tgtatcatat gtgtggatga atggaaggag tgcaaacaga aatggaagga tctcgaaaga        60

<210> SEQ ID NO 57
<211> LENGTH: 60
<212> TYPE: DNA
<213> ORGANISM: Mytilus edulis

<400> SEQUENCE: 57
aggggttcta tctctgtact tgttgtttta gcaaaagcaa tattgcatat caaacacgag        60

<210> SEQ ID NO 58
<211> LENGTH: 60
<212> TYPE: DNA
<213> ORGANISM: Mytilus edulis
```

<400> SEQUENCE: 58
gtggtagaca tattgtttgc aaagtgaagc tatgatacat cgaacatttt atgtgtagag                    60

<210> SEQ ID NO 59
<211> LENGTH: 60
<212> TYPE: DNA
<213> ORGANISM: Mytilus galloprovincialis

<400> SEQUENCE: 59
cgacactttt cattaacatc catccaacac attgtgtatc ctgttgaact acatttcata                    60

<210> SEQ ID NO 60
<211> LENGTH: 60
<212> TYPE: DNA
<213> ORGANISM: Mytilus galloprovincialis

<400> SEQUENCE: 60
gacggtatgc atcatgcaac tattggttcg caaacacatt ttacacatat tcttttatc                     60

<210> SEQ ID NO 61
<211> LENGTH: 60
<212> TYPE: DNA
<213> ORGANISM: Mytilus galloprovincialis

<400> SEQUENCE: 61
aggagtaaac atccatagat ctgagttttg agatcaaacg aggaagccta agaaatttta                    60

<210> SEQ ID NO 62
<211> LENGTH: 60
<212> TYPE: DNA
<213> ORGANISM: Mytilus galloprovincialis

<400> SEQUENCE: 62
ttattgaatt atttctgttg ccgttacgtc tgtttatcca cgagtctttt aggaatctct                    60

<210> SEQ ID NO 63
<211> LENGTH: 60
<212> TYPE: DNA
<213> ORGANISM: Mytilus galloprovincialis

<400> SEQUENCE: 63
atgtgttggc attaacattg accatatgtg ttggcattaa cattgaccat atgtgttggc                    60

<210> SEQ ID NO 64
<211> LENGTH: 60
<212> TYPE: DNA
<213> ORGANISM: Mytilus edulis

<400> SEQUENCE: 64
tggaccaggc tggctaaata tggttttcat ggctttggca tttgttttca gctgaaagac                    60

<210> SEQ ID NO 65
<211> LENGTH: 60
<212> TYPE: DNA
<213> ORGANISM: Mytilus edulis

<400> SEQUENCE: 65
cgggtaaagc tgtaaatcca caagtctttc agaataagta ggttgtatga agaattgtta                    60

<210> SEQ ID NO 66
<211> LENGTH: 60
<212> TYPE: DNA
<213> ORGANISM: Mytilus edulis

<400> SEQUENCE: 66
gaataaaatt ctttggcttc ttcgattgat ctcaaaactc agatctatgg atgtttgccc          60

<210> SEQ ID NO 67
<211> LENGTH: 60
<212> TYPE: DNA
<213> ORGANISM: Mytilus edulis

<400> SEQUENCE: 67
ggttactttg aagtaaattg agaacatgtt acctatttgt ttgttgttgg ttggacacct          60

<210> SEQ ID NO 68
<211> LENGTH: 60
<212> TYPE: DNA
<213> ORGANISM: Mytilus edulis

<400> SEQUENCE: 68
cattacggcc ggggcagaca aaacatatgg ttagatatca attgaacatt taaaatttca          60

<210> SEQ ID NO 69
<211> LENGTH: 60
<212> TYPE: DNA
<213> ORGANISM: Mytilus edulis

<400> SEQUENCE: 69
tttaggagct atcttgaact ttagtgttgt gtgagctttg ttctttcaaa ggcttcactg          60

<210> SEQ ID NO 70
<211> LENGTH: 60
<212> TYPE: DNA
<213> ORGANISM: Mytilus edulis

<400> SEQUENCE: 70
aacaagaacc gggaatgtgg tatcagctct ctaaagatga aattgttgat aaacaactta          60

<210> SEQ ID NO 71
<211> LENGTH: 60
<212> TYPE: DNA
<213> ORGANISM: Mytilus edulis

<400> SEQUENCE: 71
ggggccaaag gtcatgtgga tttgacaaca gaatcggaag aggatttatt aatagtatag          60

<210> SEQ ID NO 72
<211> LENGTH: 60
<212> TYPE: DNA
<213> ORGANISM: Mytilus galloprovincialis

<400> SEQUENCE: 72
ataacaacac ctagtcaagg actctttgga gcttttggag gtccatcttt tggaggagga          60

<210> SEQ ID NO 73
<211> LENGTH: 60
<212> TYPE: DNA
<213> ORGANISM: Mytilus galloprovincialis

<400> SEQUENCE: 73
agcgaggtta tcattattct tgacacttga ccactcacat attaaacctg catctaattt          60

<210> SEQ ID NO 74
<211> LENGTH: 60
<212> TYPE: DNA
<213> ORGANISM: Mytilus galloprovincialis

<400> SEQUENCE: 74
agagaagttt attgaggctg ttcaacaagg ggaaaatcca gagataacta aaaatgtggc    60

<210> SEQ ID NO 75
<211> LENGTH: 60
<212> TYPE: DNA
<213> ORGANISM: Mytilus galloprovincialis

<400> SEQUENCE: 75
tctgaactta ctgtctcaat tgctacgtga aatttttgtt gcaacagtta tcgtgatagc    60

<210> SEQ ID NO 76
<211> LENGTH: 60
<212> TYPE: DNA
<213> ORGANISM: Mytilus galloprovincialis

<400> SEQUENCE: 76
ctggaaccag ttgaaaaagc tttaagagac gctaaacttg ataaaagtag tattcaagag    60

<210> SEQ ID NO 77
<211> LENGTH: 60
<212> TYPE: DNA
<213> ORGANISM: Mytilus edulis

<400> SEQUENCE: 77
gtgcaatatt ataactgttg aatggtattt catttccttg cagcttgtgt gaagcaaaca    60

<210> SEQ ID NO 78
<211> LENGTH: 60
<212> TYPE: DNA
<213> ORGANISM: Mytilus galloprovincialis

<400> SEQUENCE: 78
ctgaagtcct tgttggtaca ttaaaaccgg catcttggtc gatttctttc acagaaaaaa    60

<210> SEQ ID NO 79
<211> LENGTH: 60
<212> TYPE: DNA
<213> ORGANISM: Mytilus galloprovincialis

<400> SEQUENCE: 79
tatggcagag aaagacaaag ctagatatga gggagaaaat gcaaattacg agccaggacc    60

<210> SEQ ID NO 80
<211> LENGTH: 60
<212> TYPE: DNA
<213> ORGANISM: Mytilus edulis

<400> SEQUENCE: 80
gtgtaacttt agtagaggaa aggttagtgg acaaatagtg gattacctca tatgaatgaa    60

<210> SEQ ID NO 81
<211> LENGTH: 60
<212> TYPE: DNA
<213> ORGANISM: Mytilus edulis

<400> SEQUENCE: 81
tcgacaacaa accaaccaaa cttcagatgc tgactctcag aagaataaag gaggaaaaaa    60

<210> SEQ ID NO 82
<211> LENGTH: 60
<212> TYPE: DNA
<213> ORGANISM: Mytilus galloprovincialis

```
<400> SEQUENCE: 82
actatgacaa tgacagagtt cgtgactgtt tatatctgaa ataaatcagc agatgtctcc    60

<210> SEQ ID NO 83
<211> LENGTH: 60
<212> TYPE: DNA
<213> ORGANISM: Mytilus galloprovincialis

<400> SEQUENCE: 83
cattccttgg attaatagca tcgttggaca gtaaacagtt aaatgtgctt gtttaacatg    60

<210> SEQ ID NO 84
<211> LENGTH: 60
<212> TYPE: DNA
<213> ORGANISM: Mytilus edulis

<400> SEQUENCE: 84
gacgtctgaa aagcagtaga cctgtttttt actcgcataa ttgcatctta tgtagaattt    60

<210> SEQ ID NO 85
<211> LENGTH: 60
<212> TYPE: DNA
<213> ORGANISM: Mytilus edulis

<400> SEQUENCE: 85
gcaggagcaa caacaaaagt atctctaaat caagatcaag atctcctgag taaaataaca    60

<210> SEQ ID NO 86
<211> LENGTH: 60
<212> TYPE: DNA
<213> ORGANISM: Mytilus edulis

<400> SEQUENCE: 86
tagagatggt cgagcatcac ttttctttgg ataaatcgca tgaaacagtt gcactacttt    60

<210> SEQ ID NO 87
<211> LENGTH: 60
<212> TYPE: DNA
<213> ORGANISM: Mytilus edulis

<400> SEQUENCE: 87
gtctgtttac agtgctgaat caataattgc tcttggaaca cccaaaatta aaagtgcaaa    60

<210> SEQ ID NO 88
<211> LENGTH: 60
<212> TYPE: DNA
<213> ORGANISM: Mytilus edulis

<400> SEQUENCE: 88
cgggaatagt gcaatttgtt tcgtgtgtga taaacacagt acaaaataga attgtttgca    60

<210> SEQ ID NO 89
<211> LENGTH: 60
<212> TYPE: DNA
<213> ORGANISM: Mytilus edulis

<400> SEQUENCE: 89
gtgaacgtcc aatgaccaaa gacaaccatc aacttggtaa attcgacctg actggcattc    60

<210> SEQ ID NO 90
<211> LENGTH: 60
<212> TYPE: DNA
<213> ORGANISM: Mytilus edulis
```

<400> SEQUENCE: 90
cagttgtgtt tgcatgttca tggctatcct agttatagaa ataaaaggaa tatcaagtcc    60

<210> SEQ ID NO 91
<211> LENGTH: 60
<212> TYPE: DNA
<213> ORGANISM: Mytilus edulis

<400> SEQUENCE: 91
gaatcaagac acatccctat gcaatcaaag aaaacaaact gggtttgttg tgtacataat    60

<210> SEQ ID NO 92
<211> LENGTH: 60
<212> TYPE: DNA
<213> ORGANISM: Mytilus edulis

<400> SEQUENCE: 92
tagggacttt gcggaatgtg ttgtgatatt cgtatgatta acaacactgt agtgttataa    60

<210> SEQ ID NO 93
<211> LENGTH: 60
<212> TYPE: DNA
<213> ORGANISM: Mytilus edulis

<400> SEQUENCE: 93
caatgggaga ttactctaga agtacaaata gaatgtattg gtgaccgtga tcatattaca    60

<210> SEQ ID NO 94
<211> LENGTH: 60
<212> TYPE: DNA
<213> ORGANISM: Mytilus edulis

<400> SEQUENCE: 94
cctaccttcc cacattcatc tttctgggat agtcctgaat attacttcca tgcatatatt    60

<210> SEQ ID NO 95
<211> LENGTH: 60
<212> TYPE: DNA
<213> ORGANISM: Mytilus edulis

<400> SEQUENCE: 95
tgggggatgg cccagttgct ttgatgaagc taagctcaaa agtagtttat tgctctgagt    60

<210> SEQ ID NO 96
<211> LENGTH: 60
<212> TYPE: DNA
<213> ORGANISM: Mytilus galloprovincialis

<400> SEQUENCE: 96
gggtttacta tgttcgttgt catctcatca ttgcattacc tgtgatcaag aaaaactata    60

<210> SEQ ID NO 97
<211> LENGTH: 60
<212> TYPE: DNA
<213> ORGANISM: Mytilus galloprovincialis

<400> SEQUENCE: 97
gcatatatcc attgtgctct tacagtaatt gttaacatta gacatcgttt gctacatgtg    60

<210> SEQ ID NO 98
<211> LENGTH: 60
<212> TYPE: DNA
<213> ORGANISM: Mytilus edulis

<400> SEQUENCE: 98
ctctgacaca ttgatgcatt caaacttcat gcttggtgtc ataccagtct tataaattat    60

<210> SEQ ID NO 99
<211> LENGTH: 60
<212> TYPE: DNA
<213> ORGANISM: Mytilus edulis

<400> SEQUENCE: 99
ctgacaatga cacaatgaca gcatattttg cattttcagt acagatgggt atgttgtata    60

<210> SEQ ID NO 100
<211> LENGTH: 60
<212> TYPE: DNA
<213> ORGANISM: Mytilus edulis

<400> SEQUENCE: 100
gcattgctga ttcggtttct cgaaaactgt gtaacatttc atactgaca atcattattc    60

<210> SEQ ID NO 101
<211> LENGTH: 60
<212> TYPE: DNA
<213> ORGANISM: Mytilus edulis

<400> SEQUENCE: 101
ttggcttcca acatgtctgt gcagaattca tacgttatta cagaacatga tgttatacat    60

<210> SEQ ID NO 102
<211> LENGTH: 60
<212> TYPE: DNA
<213> ORGANISM: Mytilus edulis

<400> SEQUENCE: 102
cgagcttatg atatcatgac catgctgtat cttttcata ccatttgtac ctcggccgcg    60

<210> SEQ ID NO 103
<211> LENGTH: 60
<212> TYPE: DNA
<213> ORGANISM: Mytilus galloprovincialis

<400> SEQUENCE: 103
attgaagtct gtcagcagac caaaataat atgcttgctg taatggaaat aacttactgc    60

<210> SEQ ID NO 104
<211> LENGTH: 60
<212> TYPE: DNA
<213> ORGANISM: Mytilus galloprovincialis

<400> SEQUENCE: 104
atcagttgat catcagagaa tcacattcag aagctcgtga agctaatcaa gctacacaaa    60

<210> SEQ ID NO 105
<211> LENGTH: 60
<212> TYPE: DNA
<213> ORGANISM: Mytilus galloprovincialis

<400> SEQUENCE: 105
gtgtggagcc aattcaagag atagggttgg aaagatttat aaaatccaaa ttgctggaat    60

<210> SEQ ID NO 106
<211> LENGTH: 60
<212> TYPE: DNA
<213> ORGANISM: Mytilus galloprovincialis

```
<400> SEQUENCE: 106
atgttgacat gtcatctgat gattctgatg aagaaacacc tcaaaccacc aagtctggta      60

<210> SEQ ID NO 107
<211> LENGTH: 60
<212> TYPE: DNA
<213> ORGANISM: Mytilus edulis

<400> SEQUENCE: 107
aataaaagtt tgacaacagc taaatcctat actccaactc agaccccacc acactgtgtt      60

<210> SEQ ID NO 108
<211> LENGTH: 60
<212> TYPE: DNA
<213> ORGANISM: Mytilus edulis

<400> SEQUENCE: 108
tctcatagtt taacaagaag cggttataat ctgatcgtta ctgtaaaaaa tagtccggag      60

<210> SEQ ID NO 109
<211> LENGTH: 60
<212> TYPE: DNA
<213> ORGANISM: Mytilus edulis

<400> SEQUENCE: 109
cggtgtcatg tgcgtctgtt acttttgata tttcagatac tcgtgtaatg cgtacctcgg      60

<210> SEQ ID NO 110
<211> LENGTH: 60
<212> TYPE: DNA
<213> ORGANISM: Mytilus edulis

<400> SEQUENCE: 110
cccattttta taaactgctt tattttcaag tgtaaactgt ctttatgtac ctcggccgcg      60

<210> SEQ ID NO 111
<211> LENGTH: 60
<212> TYPE: DNA
<213> ORGANISM: Mytilus edulis

<400> SEQUENCE: 111
gaatattcat tgtgtgacac agaggtcact ctaaaaatgt ctcactgttt tcttactcat      60

<210> SEQ ID NO 112
<211> LENGTH: 60
<212> TYPE: DNA
<213> ORGANISM: Mytilus galloprovincialis

<400> SEQUENCE: 112
cgaacaagtg acatatgcag ttactattgc gtaatagtcc agacatttat agaacattag      60

<210> SEQ ID NO 113
<211> LENGTH: 60
<212> TYPE: DNA
<213> ORGANISM: Mytilus galloprovincialis

<400> SEQUENCE: 113
gcagcttagt aaggtgtgtc taatttattt gggagaaatc ctttgtgttt gtttgtaatg      60

<210> SEQ ID NO 114
<211> LENGTH: 60
<212> TYPE: DNA
<213> ORGANISM: Mytilus galloprovincialis
```

<400> SEQUENCE: 114
cgagaaattg aaaggaaatt catgttgacc tttcaaaatg acacacttc aggaaatcat    60

<210> SEQ ID NO 115
<211> LENGTH: 60
<212> TYPE: DNA
<213> ORGANISM: Mytilus galloprovincialis

<400> SEQUENCE: 115
ctaaaaacag aggaagccaa tactttaaga aagaaaacta cagcaaggca aagcagttct    60

<210> SEQ ID NO 116
<211> LENGTH: 60
<212> TYPE: DNA
<213> ORGANISM: Mytilus galloprovincialis

<400> SEQUENCE: 116
cttgtttgaa agccgtcagt ttgtcgaact tctgcatgct acttttggtg caaaggttga    60

<210> SEQ ID NO 117
<211> LENGTH: 60
<212> TYPE: DNA
<213> ORGANISM: Mytilus galloprovincialis

<400> SEQUENCE: 117
aacgcaaatt tatccaagat gtgggcctgg ggattcgtta tattacaata attcttgtta    60

<210> SEQ ID NO 118
<211> LENGTH: 60
<212> TYPE: DNA
<213> ORGANISM: Mytilus galloprovincialis

<400> SEQUENCE: 118
gaagcggtta aacgcatgtg tgttcattta tgacaattaa gaaatttatc gaaagtggtg    60

<210> SEQ ID NO 119
<211> LENGTH: 60
<212> TYPE: DNA
<213> ORGANISM: Mytilus galloprovincialis

<400> SEQUENCE: 119
ggcttcacat gcctttgaac aatcaaaaac atggaatcgt atggcaattg gttaattatt    60

<210> SEQ ID NO 120
<211> LENGTH: 60
<212> TYPE: DNA
<213> ORGANISM: Mytilus galloprovincialis

<400> SEQUENCE: 120
ggagacataa aatctacacc agtaaccaca ttatgcaagg gatacattac attctgctga    60

<210> SEQ ID NO 121
<211> LENGTH: 60
<212> TYPE: DNA
<213> ORGANISM: Mytilus edulis

<400> SEQUENCE: 121
gtgaatatat cagatcttcg aggcacacgt gattagactt aagttcatat tcgtgatata    60

<210> SEQ ID NO 122
<211> LENGTH: 60
<212> TYPE: DNA
<213> ORGANISM: Mytilus edulis

```
<400> SEQUENCE: 122 catgaccccgc aatagtgtcg caaacgaaag taagttacat ttaaaagaat ggaggaagaa      60
```

METHODS AND PROBES FOR MONITORING MARINE WATER

CROSS REFERENCE TO RELATED APPLICATIONS

This application is a National Stage of International Application No. PCT/IB2014/063481, filed 28 Jul. 2014 and U.S. Provisional Patent Application No. 61/861,842, filed 2 Aug. 2013, both entitled "METHODS AND PROBES FOR MONITORING MARINE WATER". The entire contents of each of the above-identified prior applications are hereby incorporated by reference."

SEQUENCE LISTING

The instant application contains a Sequence Listing which has been submitted electronically in ASCII format and is hereby incorporated by reference in its entirety. Said ASCII copy, created on Feb. 11, 2016, is named VIU002-US_SL.txt and is 18,542 bytes in size.

BACKGROUND OF THE INVENTION

Field of the Invention

The present technology relates to probes and methods of use thereof for monitoring aquatic environmental quality. More specifically, the technology relates to *Mytilus edulis* and *Mytilus galloprovincialis* probes and methods of use thereof to quantify stress levels in these invertebrates as a measure of anthropogenic or environmental variables in the water.

Description of the Related Art

Ocean coastlines around the world are under increasing pressure from urbanization, industry, recreation, aquaculture and climate change impacts. The presence of stressing agents from environmental, for example, but not limited to, temperature, salinity, food availability, or oxygen levels, biological, (for example, but not limited to bacteria or toxic algae) and anthropogenic sources; (for example, but not limited to wastewater, pollution, poor resource management or aquaculture practices) can affect the marine environment. These pressures require effective diagnostic tools to continually monitor coastal ecosystem health and function. Shellfish are a critical part of coastal and estuarine ecosystems and as sessile, filter-feeding animals, act as the "canary in the coalmine" of our coastal environment, providing a living warning of dangers to people on our coasts where human populations are concentrated. In North America, three such shellfish—mussels, oysters and Zebra mussels—have become sentinel or indicator species for monitoring environmental quality on the Pacific and Atlantic coasts from Alaska to Hawaii and from the Great Lakes to Puerto Rico. This "Mussel Watch" program has run continuously since 1986, includes 300 active monitoring sites and assesses 140 contaminants. Because shellfish are well distributed along coasts and are sessile, they are better integrators of contaminants in any given area. They are good indicators for environmental quality because their tissues respond to changes in ambient environmental levels, their wide geographical distribution, and their sessile nature make them excellent in situ bioaccumulators of pollution, providing valuable information on changes in coastal environments.

The global market for instrumentation to test and monitor wastewater is expected to reach $10 billion by 2016 as regulations in all jurisdictions become increasingly stringent and enforcement mechanisms improve. The Canadian economy relies heavily on fish and seafood—in 2004 these aquatic resources were the single largest export food commodity, by value, in Canada. Canada is the fifth largest seafood exporter in the world with more than $4.3 billion in value in 2005.

Uses of indicator species, as currently practised through well established programs like Mussel Watch, have become standard practice for monitoring the receiving environment. However, most of the analysis techniques rely on physical and chemical tests of the animal tissues, which are extremely slow and inefficient, and provide limited information on animal health and function.

In the US, biomonitoring is required under National Pollution Discharge Elimination System permits, which may include freshwater, marine or estuarine species. Facilities that process over a million gallons of wastewater per day are required to test water samples daily for toxicity and smaller facilities typically run these tests monthly. Effluent bioassays, biomonitoring and Whole Effluent Toxicity (WET) testing are all terms used to describe testing of wastewater discharge with aquatic organisms to assess the discharge's toxicity. WET tests are today's most common test for toxicity, but provide no information on the biological impacts of toxicity levels in ecosystems. In a WET test, organisms are exposed to various effluent concentrations for a specified time period in order to estimate toxicity. Sewage outflow water is used in the laboratory to simulate what happens in the natural environment. The most commonly used organisms for these tests are fathead minnows and an invertebrate—*Ceriodapahnia dubia*. Acute tests measure the concentration of test material that produces a lethal outcome during a 48-96 hour period. Chronic tests estimate the concentration of effluent that interferes with growth, development and reproduction over 4-7 days—the life cycle or life stage of the organism. WET tests average about $100/test in the US market.

When WET tests reveal the presence of a toxin and that toxin requires further identification, then the waste water facility must conduct a TIE and/or TRE study. A TRE—Toxicity Reduction Evaluation—is a systematic evaluation of the wastewater effluents to determine sources of toxicity and how to control this. This may include chemical screens, process reviews, evaluation of the facility's process performance and TIE—Toxicity Identification Evaluation. The objective of TIE is to characterize and identify the compound(s) causing toxicity. In TIE, effluent samples are manipulated to remove suspect chemicals and then re-test them to see if the toxicity remains, which provides clues to the analyst as to the source of the toxicity. TIE tests typically cost $1,000 each in the US market.

According to a Chief Plant Operator at a US waste water treatment plant, "it makes sense to offer a test similar to WET, but that is able to gather more nuanced information . . . at the depth offered by molecular analysis. End-users may find a new type of toxicity testing appealing if it were capable of gathering data on components beyond those for which testing is currently mandated. Other components of interest include: metals, chemical toxins, microbes, hormones or pharmaceuticals. A new method should be able to detect the presence of these components in trace amounts. End-users at water treatment plants may be interested in a micro-array if it can somehow identify toxins early, in a way that prevents drastic follow-up attempts to purify the water in the presence of toxins. If it could be demonstrated that this test can help prevent problems with toxins before reactionary methods become necessary, then end-users may be willing to purchase this type of technology before it is mandated by EPA." A Lab Manager in the Ecology Division of a US environmental consulting firm, said that "one near-term application that may not require EPA approval is to use this new technology to reduce the number of TIE procedures that have to be performed once a toxin has been identified. If the new technology could reduce the number of TIE tests required to isolate toxins, then this would save companies time and money."

At present tools for wastewater management using bivalves include visual indicators of acute and chronic mortality phases and other indicators such as shell growth, which have proven to be highly variable and therefore not always informative. To assess the effects of contaminants, histology assays have been developed that include the evaluation of lysosomal membrane stability and response indices. Biochemical assays include acetylcholinesterase activity, metallothionein content, vitellogenin, superoxidase dismutase, glutathione peroxidase levels and the accumulation of heat shock proteins. These assays are relatively difficult, time consuming to conduct, and each test provides information on only the end point of one gene which limits their usefulness in environmental monitoring. In addition, analysis of pollutant concentrations in sediments provides information on contamination levels, but not the effects on organism function, and benthic biodiversity analysis provides information of detrimental impacts only after community structure has shifted.

Microarrays have been used to measure gene expression in many systems. This is more sensitive than measuring biomarkers at the protein level. Analysis of gene expression profiles is increasingly used to evaluate the biological effects of stress on aquatic animals. Using Reverse Transcription real-time quantitative Polymerase Chain Reaction (qRT-PCR) in mussel studies, only limited numbers of genes have been examined, for example five genes from *M. galloprovincialis* in Li et al., 2010 ("Expression of *Mytilus* immune genes in response to experimental challenges varied according to the site of collection." Fish & Shellfish Immunology 28(4): 640-648), five in Veldhoen et al., 2011 ("Relationship between mRNA biomarker candidates and location near a marine municipal wastewater outfall in the benthic indicator species *Modiolus modiolus* (L.)." Aquatic Toxicology 105 (1-2): 119-126) and twelve in Veldhoen et al., 2009 ("Gene expression profiling in the deep water horse mussel *Modiolus modiolus* (L.) located near a marine municipal wastewater outfall." Aquatic Toxicology 93(2-3): 116-124) from *Modiolus modiolus*.

There is a need to improve environmental monitoring in coastal waters. Testing methods should be rapid, accurate and inexpensive. It would be advantageous to have a suite of biomarkers to facilitate a comprehensive understanding of organism health as it relates to the health of marine environments. These could then be employed to monitor the marine environment. It would also be advantageous if the biomarkers could support versioning to keep current and meet commercial market requirements, have broad global species coverage and have the capability to monitor a broad range of environmental stressors.

SUMMARY OF THE INVENTION

The present technology provides a rapid, accurate and inexpensive testing tool for monitoring environmental quality of coastal waters. Specifically, a multi-species oligo-microarray designed for utilization in the assessment of stress responses in marine mussels is provided that supports versioning to keep current and meet commercial market requirements, has broad global species coverage and has the capability to monitor a broad range of environmental stressors. Sequences on this array consist of genes involved in stress responses to thermal shock, hypoxia, salinity, bacterial challenges and physical disturbances. This microarray allows the determination of stress responses in at least two of the world's most widely distributed species of marine mussels—*Mytilus edulis* and *Mytilus galloprovincialis*, in addition to *Mytilus trossulus*—*Mytilus* species that are found world-wide.

In one embodiment, a kit for monitoring environmental health of marine water is provided, the kit comprising a plurality of probes, the probes consisting of at least 20 consecutive nucleotides of at least 50 sequences of SEQ ID NO: 1-122 and a suitably selected buffer.

In the kit, the probes may be in a microarray.

In the kit, the probes may be selected from SEQ ID NO: 1, 3, 5-10, 16, 30, 32-34, 36, 39, 43-44, 46, 49-50, 54-56, 58-59, 61-63, 65, 69, 71-74, 76-78, 87, 89-92, 95-96, 99, 101, 107-110, 114, 121-122.

In the kit, the probes may consist of at least 40 consecutive nucleotides.

The kit may comprise at least 80 sequences.

In the kit, the probes may consist of at least 60 consecutive nucleotides.

A set of probes for detecting physical or temperature stress in marine mussels is also provided. The probes consist of at least 20 consecutive nucleotides of at least 50 sequences of SEQ ID NO: 1-122.

In the set, the probes may consist of at least 40 consecutive nucleotides.

The set may comprise at least 80 sequences.

In the set, the probes consist of at least 60 consecutive nucleotides.

In the set, the probes may be selected from SEQ ID NO: 2-5, 8, 10, 15, 21-25, 27, 35, 36, 48-41, 42, 43, 45-47, 51, 56, 57, 63, 64, 70-72, 74, 76, 79, 81, 83, 85, 89, 90, 97, 100, 107, 108, 111-113, and 115-117.

In the set, the probes may be *Mytilus edulis* probes.

In another embodiment, a use of the set of probes described above for monitoring marine water is provided.

In another embodiment, a method of biomonitoring marine water is provided, the method comprising: extracting messenger Ribonucleic Acid (mRNA) from *Mytilus* species; preparing cDNA from the mRNA; hybridizing a plurality of probes with the cDNA to provide a set of hybridized cDNA, the probes consisting of at least 20 consecutive nucleotides of at least 50 sequences of SEQ ID NO: 1-122; and quantifying an abundance of the set of hybridized cDNA, thereby biomonitoring marine water.

In the method, the probes may be in a reverse transcription real-time quantitative PCR assay.

In the method, the probes may consist of at least 30 consecutive nucleotides.

In the method, the probes may consist of 122 sequences of SEQ ID NO: 1-122.

In the method, the probes may consist of 60 consecutive nucleotides.

In the method, the probes may be selected from SEQ ID NO: 1, 3, 5-10, 16, 30, 32-34, 36, 39, 43-44, 46, 49-50, 54-56, 58-59, 61-63, 65, 69, 71-74, 76-78, 87, 89-92, 95-96, 99, 101, 107-110, 114, 121-122.

In the method, the probes may be *Mytilus edulis* probes.

BRIEF DESCRIPTION OF THE DRAWINGS

FIG. 1 shows Real-time qPCR validations of Myt-OME microarray data for heat shock protein in mussel digestive gland (hsp70) over time (time 0-24 hours) using the present technology.

FIG. 2 shows Real-time qPCR validations of Myt-OME microarray data for sequestosome genes in gill tissues over time (time 0-24 hours) using the present technology.

BRIEF DESCRIPTION OF THE SEQUENCES

SEQ ID NO 1: unclassified *Mytilus edulis*
SEQ ID NO 2: Poly [ADP-ribose] polymerase 14 (EC 2.4.2.30) (PARP-14) (B aggressive lymphoma protein 2). n=2 Tax=*Canis lupus familiaris* RepID=UPI0000EB038A *Mytilus edulis*
SEQ ID NO 3: Heat shock protein 70 n=5 Tax=*Mytilus galloprovincialis* RepID=Q3LF66_MYTGA *Mytilus edulis*
SEQ ID NO 4: proteophosphoglycan 5 *Mytilus edulis*
SEQ ID NO 5: PREDICTED: dual specificity phosphatase 10-like n=1 Tax=*Saccoglossus kowalevskii* RepID=UPI0001CB982B *Mytilus edulis*
SEQ ID NO 6: unclassified *Mytilus edulis*
SEQ ID NO 7: unclassified *Mytilus edulis*
SEQ ID NO 8: Small 22 kd heat shock protein n=1 Tax=*Chlamys farreri* RepID=Q6USC0_9 BIVA *Mytilus edulis*
SEQ ID NO 9: unclassified *Mytilus edulis*
SEQ ID NO 10: PREDICTED: similar to predicted protein n=1 Tax=*Hydra magnipapillata* RepID=UPI00019260BB *Mytilus galloprovincialis*
SEQ ID NO 11: unclassified *Mytilus edulis*
SEQ ID NO 12: unclassified *Mytilus edulis*
SEQ ID NO 13: unclassified *Mytilus edulis*
SEQ ID NO 14: unclassified *Mytilus edulis*
SEQ ID NO 15: Chaperone protein DNAj, putative n=2 Tax=*Trypanosoma brucei* RepID=D0A5P1_TRYBG *Mytilus edulis*
SEQ ID NO 16: unclassified *Mytilus edulis*
SEQ ID NO 17: unclassified *Mytilus edulis*
SEQ ID NO 18: unclassified *Mytilus edulis*
SEQ ID NO 19: unclassified *Mytilus edulis*
SEQ ID NO 20: unclassified *Mytilus galloprovincialis*
SEQ ID NO 21: Universal stress protein G *Mytilus galloprovincialis*
SEQ ID NO 22: Serine protease inhibitor CFSPI3 n=1 Tax=*Chlamys farreri* RepID=A0S0Q1_9 BIVA *Mytilus galloprovincialis*
SEQ ID NO 23: PREDICTED: similar to RuvB-like DNA helicase TIP49b n=1 Tax=*Monodelphis domestica* RepID=UPI0000F2D4A1 *Mytilus galloprovincialis*
SEQ ID NO 24: unclassified *Mytilus edulis*
SEQ ID NO 25: PREDICTED: splicing factor, arginine/serine-rich 2-like n=1 Tax=*Saccoglossus kowalevskii* RepID=UPI0001CB96F6 *Mytilus edulis*
SEQ ID NO 26: unclassified *Mytilus edulis*
SEQ ID NO 27: TFIIF_alpha multi-domain protein *Mytilus edulis*
SEQ ID NO 28: unclassified *Mytilus edulis*
SEQ ID NO 29: unclassified *Mytilus edulis*
SEQ ID NO 30: unclassified *Mytilus edulis*
SEQ ID NO 31: unclassified *Mytilus galloprovincialis*
SEQ ID NO 32: unclassified *Mytilus galloprovincialis*
SEQ ID NO 33: unclassified *Mytilus galloprovincialis*
SEQ ID NO 34: unclassified *Mytilus galloprovincialis*
SEQ ID NO 35: PREDICTED: chaperonin containing TCP1, subunit 2-like n=1 Tax=*Saccoglossus kowalevskii* RepID=UPI0001CBA14F *Mytilus edulis*
SEQ ID NO 36: PREDICTED: similar to Phosphoenolpyruvate carboxykinase 2 (mitochondrial) n=2 Tax=*Strongylocentrotus purpuratus* RepID=UPI0000E4979D *Mytilus galloprovincialis*
SEQ ID NO 37: unclassified *Mytilus edulis*
SEQ ID NO 38: Dopamine beta hydroxylase-like protein (Fragment) n=1 Tax=*Pomatoceros lamarckii* RepID=D2WL91_9 ANNE *Mytilus edulis*
SEQ ID NO 39: Cebpg, C/EBP[g], C/EBPgamma, GPE1-BP, Gpe1bp, Ig/EBP; CCAAT/enhancer binding protein (C/EBP), gamma; K10049 CCAAT/enhancer binding protein (C/EBP), gamma *Mytilus edulis*
SEQ ID NO 40: Prolyl 4-hydroxylase alpha subunit 1, putative n=1 Tax=*Aedes aegypti* RepID=Q1DH25_AEDAE *Mytilus edulis*
SEQ ID NO 41: PREDICTED: dynein light chain LC8-type 2 n=1 Tax=*Bos taurus* RepID=UPI00017C3AA6 *Mytilus edulis*
SEQ ID NO 42: unclassified *Mytilus edulis*
SEQ ID NO 43: PREDICTED: cysteine and histidine-rich domain (CHORD)-containing, zinc-binding protein 1-like n=1 Tax=*Saccoglossus kowalevskii* RepID=UPI0001CBA045 *Mytilus edulis*
SEQ ID NO 44: unclassified *Mytilus edulis*
SEQ ID NO 45: GK10996 gene product from transcript GK10996-RA *Mytilus edulis*
SEQ ID NO 46: similar to cytoskeleton associated protein 1 *Mytilus edulis*
SEQ ID NO 47: Groucho protein n=1 Tax=*Saccoglossus kowalevskii* RepID=B5THN7_SACKO *Mytilus edulis*
SEQ ID NO 48: unclassified *Mytilus edulis*
SEQ ID NO 49: unclassified *Mytilus edulis*
SEQ ID NO 50: unclassified *Mytilus edulis*
SEQ ID NO 51: similar to kazrin *Mytilus edulis*
SEQ ID NO 52: unclassified *Mytilus galloprovincialis*
SEQ ID NO 53: unclassified *Mytilus galloprovincialis*
SEQ ID NO 54: unclassified *Mytilus edulis*
SEQ ID NO 55: unclassified *Mytilus edulis*
SEQ ID NO 56: Hexokinase n=2 Tax=*Crassostrea gigas* RepID=Q0KHB5_CRAGI
*Mytilus edulis*
SEQ ID NO 57: Inositol-3-phosphate synthase 1-A n=4 Tax=*Xenopus* RepID=INO1A_XENLA *Mytilus edulis*
SEQ ID NO 58: unclassified *Mytilus edulis*
SEQ ID NO 59: unclassified *Mytilus galloprovincialis*
SEQ ID NO 60: unclassified *Mytilus galloprovincialis*
SEQ ID NO 61: unclassified *Mytilus galloprovincialis*
SEQ ID NO 62: unclassified *Mytilus galloprovincialis*
SEQ ID NO 63: Heat shock protein 70 n=5 Tax=*Mytilus galloprovincialis* RepID=Q3LF66_MYTGA *Mytilus galloprovincialis*
SEQ ID NO 64: PREDICTED: similar to CG9117 CG9117-PA n=1 Tax=*Danio rerio* RepID=UPI0000F1E811 *Mytilus edulis*
SEQ ID NO 65: unclassified *Mytilus edulis*
SEQ ID NO 66: unclassified *Mytilus edulis*
SEQ ID NO 67: unclassified *Mytilus edulis*
SEQ ID NO 68: unclassified *Mytilus edulis*
SEQ ID NO 69: unclassified *Mytilus edulis*
SEQ ID NO 70: PREDICTED: EKN1-like n=1 Tax=*Saccoglossus kowalevskii* RepID=UPI0001CB9891 *Mytilus edulis*
SEQ ID NO 71: OTU-like cysteine protease *Mytilus edulis*
SEQ ID NO 72: sqstm1, MGC64432; sequestosome 1 *Mytilus galloprovincialis*
SEQ ID NO 73: unclassified *Mytilus galloprovincialis*

SEQ ID NO 74: Inhibitor of apoptosis protein n=1 Tax=*Penaeus monodon* RepID=B0EVJ1_PENMO *Mytilus galloprovincialis*
SEQ ID NO 75: unclassified *Mytilus galloprovincialis*
SEQ ID NO 76: Heat shock protein 70 n=1 Tax=*Mytilus galloprovincialis* RepID=Q4W8C7_MYTGA *Mytilus galloprovincialis*
SEQ ID NO 77: unclassified *Mytilus edulis*
SEQ ID NO 78: transcriptional factor nfil3/e4bp4, putative n=1 Tax=*Pediculus humanus corporis* RepID=UPI000186D750 *Mytilus galloprovincialis*
SEQ ID NO 79: PREDICTED: similar to HMGB2 protein n=1 Tax=Pan troglodytes RepID=UPI0000E20675 *Mytilus galloprovincialis*
SEQ ID NO 80: unclassified *Mytilus edulis*
SEQ ID NO 81: PREDICTED: similar to CG11148-PA, isoform A isoform 1 n=1 Tax=*Apis mellifera* RepID=UPI0000DB7318 *Mytilus edulis*
SEQ ID NO 82: unclassified *Mytilus galloprovincialis*
SEQ ID NO 83: Trypsin-like serine protease n=1 Tax=*Periserrula leucophryna* RepID=Q6XMP3_PERLU *Mytilus galloprovincialis*
SEQ ID NO 84: unclassified *Mytilus edulis*
SEQ ID NO 85: PREDICTED: splicing factor, arginine/serine-rich 2-like n=1 Tax=*Saccoglossus kowalevskii* RepID=UPI0001CB96F6 *Mytilus edulis*
SEQ ID NO 86: unclassified *Mytilus edulis*
SEQ ID NO 87: unclassified *Mytilus edulis*
SEQ ID NO 88: unclassified *Mytilus edulis*
SEQ ID NO 89: 78 kDa glucose regulated protein n=1 Tax=*Crassostrea gigas* RepID=Q75W49_CRAGI *Mytilus edulis*
SEQ ID NO 90: Growth arrest and DNA-damage-inducible alpha-like protein n=1 Tax=Crassostrea *angulata* RepID=C8BLQ2_9 BIVA *Mytilus edulis*
SEQ ID NO 91: unclassified *Mytilus edulis*
SEQ ID NO 92: unclassified *Mytilus edulis*
SEQ ID NO 93: unclassified *Mytilus edulis*
SEQ ID NO 94: unclassified *Mytilus edulis*
SEQ ID NO 95: unclassified *Mytilus edulis*
SEQ ID NO 96: unclassified *Mytilus galloprovincialis*
SEQ ID NO 97: PREDICTED: similar to growth arrest and DNA damage 45 gamma like n=1 Tax=*Danio rerio* RepID=UPI0000F20BBD *Mytilus galloprovincialis*
SEQ ID NO 98: unclassified *Mytilus edulis*
SEQ ID NO 99: unclassified *Mytilus edulis*
SEQ ID NO 100: PREDICTED: similar to growth arrest and DNA damage 45 gamma like n=1 Tax=*Danio rerio* RepID=UPI0000F20BBD *Mytilus edulis*
SEQ ID NO 101: unclassified *Mytilus edulis*
SEQ ID NO 102: unclassified *Mytilus edulis*
SEQ ID NO 103: unclassified *Mytilus galloprovincialis*
SEQ ID NO 104: unclassified *Mytilus galloprovincialis*
SEQ ID NO 105: unclassified *Mytilus galloprovincialis*
SEQ ID NO 106: unclassified *Mytilus galloprovincialis*
SEQ ID NO 107: Kruppel-like factor n=1 Tax=*Lehmannia valentiana* RepID=Q2PHB0_9 PULM *Mytilus edulis*
SEQ ID NO 108: Sulfatase 1B (Fragment) n=1 Tax=*Haliotis discus discus* RepID=B6RB91_HALDI *Mytilus edulis*
SEQ ID NO 109: unclassified *Mytilus edulis*
SEQ ID NO 110: unclassified *Mytilus edulis*
SEQ ID NO 111: Cell division cycle 42-like protein n=1 Tax=*Philodina roseola* RepID=B6S339_9 BILA *Mytilus edulis*
SEQ ID NO 112: Growth arrest and DNA-damage-inducible alpha-like protein n=1 Tax=*Crassostrea angulata* RepID=C8BLQ2_9 BIVA *Mytilus galloprovincialis*
SEQ ID NO 113: PREDICTED: similar to serine/threonine kinase n=1 Tax=*Ornithorhynchus anatinus* RepID=UPI0001555FE9 *Mytilus galloprovincialis*
SEQ ID NO 114: unclassified *Mytilus galloprovincialis*
SEQ ID NO 115: FK506-binding protein 4 n=1 Tax=*Osmerus mordax* RepID=C1BKB3_OSMMO *Mytilus galloprovincialis*
SEQ ID NO 116: Kruppel-like factor (Fragment) n=1 Tax=*Haliotis diversicolor* RepID=B3SNT3_HALDV *Mytilus galloprovincialis*
SEQ ID NO 117: Zgc: 172053 protein n=2 Tax=*Danio rerio* RepID=A9JRA9_DANRE *Mytilus galloprovincialis*
SEQ ID NO 118: unclassified *Mytilus galloprovincialis*
SEQ ID NO 119: unclassified *Mytilus galloprovincialis*
SEQ ID NO 120: unclassified *Mytilus galloprovincialis*
SEQ ID NO 121: unclassified *Mytilus edulis*
SEQ ID NO 122: unclassified *Mytilus edulis*

DESCRIPTIONS OF THE PREFERRED EMBODIMENTS

Definitions

As used herein, a microarray, also known as a DNA microarray, gene chip, DNA chip or biochip, is a collection of microscopic DNA spots attached to a solid surface and used to measure the expression levels of large numbers of genes simultaneously. Each DNA spot contains picomoles ($10^{-12}$ moles) of a specific DNA sequence, known as probes.

As used herein, two polynucleotides are said to be capable of specifically hybridizing to one another if the two molecules are capable of forming an anti-parallel, double-stranded nucleic acid structure. A polynucleotide is said to be the "complement" of another polynucleotide if the molecules exhibit complete complementarity. As used herein, molecules are said to exhibit "complete complementarity" when every nucleotide in each of the polynucleotides is complementary to the corresponding nucleotide of the other. Two polynucleotides are said to be "minimally complementary" if they can hybridize to one another with sufficient stability to permit them to remain annealed to one another under at least conventional "low-stringency" conditions. Similarly, the polynucleotides are said to be "complementary" if they can hybridize to one another with sufficient stability to permit them to remain annealed to one another under conventional "high-stringency" conditions. Conventional stringency conditions are known to those skilled in the art and can be found, for example in Molecular Cloning: A Laboratory Manual, 3.sup.rd edition Volumes 1, 2, and 3. J. F. Sambrook, D. W. Russell, and N. Irwin, Cold Spring Harbor Laboratory Press, 2000.

Departures from complete complementarity are therefore permissible, as long as such departures do not completely preclude the capacity of the polynucleotides to form a double-stranded structure. Thus, in order for a polynucleotide to serve as a primer or probe it need only be sufficiently complementary in sequence to be able to form a stable double-stranded structure under the particular solvent and salt concentrations employed. Appropriate stringency conditions which promote DNA hybridization are, for example, 6.0× sodium chloride/sodium citrate (SSC) at about 45° C., followed by a wash of 2.0×SSC at 50° C. Such conditions are known to those skilled in the art and can be found, for example in Current Protocols in Molecular Biology, John Wiley & Sons, N.Y. (1989). Salt concentration and temperature in the wash step can be adjusted to alter hybridization stringency. For example, conditions may vary from low stringency of about 2.0×SSC at 40° C. to moderately stringent conditions of about 2.0×SSC at 50° C. to high stringency conditions of about 0.2×SSC at 50° C.

As used herein "sequence identity" refers to the extent to which two optimally aligned polynucleotides or polypeptide sequences are invariant throughout a window of alignment of components, e.g. nucleotides or amino acids. An "identity fraction" for aligned segments of a test sequence and a reference sequence is the number of identical components which are shared by the two aligned sequences divided by the total number of components in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as those in the BLAST suite of sequence analysis programs.

The target molecules are nucleotides (including oligonucleotides) or polypeptides, which are capable of binding to specific probes, such as complementary nucleic acids. The probes may be immobilized, e.g. by covalent or non-covalent bonding, to the surface in small amounts of substantially purified and isolated molecules in a grid pattern. By immobilized it is meant that the probe molecules maintain their position relative to the solid support under hybridization and washing conditions. Probe molecules are deposited in small footprint, isolated quantities of "spotted elements" of preferably single-stranded polynucleotide preferably arranged in rectangular grids in a density of about 30 to 100 or more, e.g. up to about 1000, spotted elements per square centimeter. In one embodiment of the invention, the arrays comprise at least about 100 or more, e.g. at least about 1000 to 5000, distinct probes per unit substrate. Where detection of transcription for a large number of genes is desired, the economics of arrays favors a high density design criteria provided that the probe molecules are sufficiently separated so that the intensity of the indicia of a binding event associated with highly expressed mRNA does not overwhelm and mask the indicia of neighboring binding events. For high-density microarrays each spotted element may contain up to about $10^7$ or more copies of the probe molecule, e.g. single stranded cDNA, on glass substrates or nylon substrates.

Arrays of this invention may be prepared with molecules from one or more species. Arrays with probe molecules from a single species can be used with mRNA from the same species or a different species due to the ability of cross species homologous genes to hybridize. It is generally preferred for high stringency hybridization that the mRNA and probe molecules are from the same species.

In one embodiment of the invention, the probes have at least about 80 percent sequence identity to the corresponding sequence selected from the group consisting of SEQ ID NO: 1 through SEQ ID NO: 122 or complements thereof. In another embodiment of the invention, at least about 10% of the probe molecules on an array have at least about 15 consecutive nucleotides of sequence having at least about 80% and up to about 100% identity with a corresponding sequence selected from the group consisting of SEQ ID NO: 1 through SEQ ID NO: 122 or complements or fragments thereof.

The array of the present technology has a total of 15,744 spots (or features on the array), of which 15,028 were annotated spots corresponding to the probe sequences. cDNA arrays: In the context of the present technology "c" refers to complimentary. oDNA arrays: In the context of the present technology "o" refers to oligonucleotide. As used herein, "preparing" refers to any method of reverse transcription of mRNA to cDNA, including, but not limited to, chemical synthesis, enzyme-mediated synthesis, hybridization and PCR.

As used herein, "marine waters" refers to any environment in which marine mussels can survive. This includes, but is not limited to coastal regions, estuaries, salt water lagoons, laboratory aquariums, offshore farms, coastal farms, and offshore colonies. "Marine water", therefore includes, but is not limited to, salt water, brackish water, brine, artificial ocean water and artificial brackish water.

Description

Except as otherwise expressly provided, the following rules of interpretation apply to this specification (written description, claims and drawings): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, The terms "comprising," "having," "including," and "containing" are to be construed as open-ended terms (i.e., meaning "including, but not limited to,") unless otherwise noted.

To the extent necessary to provide descriptive support, the subject matter and/or text of the appended claims is incorporated herein by reference in their entirety. Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

All methods described herein can be performed in any suitable order unless otherwise indicated herein or otherwise clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Example 1: cDNA Library Generation

As there was little genomic information available for the two species of interest at the project onset, it was necessary to develop this under the project. A combination of highly normalized and suppression subtraction hybridization (SSH) cDNA libraries were generated in order to maximize efficiencies of identifying genes, including rare transcripts, that may be involved in the stress responses of marine mussels. In total five cDNA libraries were generated from different mussel tissues following stress exposures. Fully acclimatized populations of mussels were held in optimal conditions at the Centre for Shellfish Research (CSR) and were then exposed to relevant stressors; temperature shock (increase), hypoxia, physical disturbance, salinity shock (decrease) and biological challenge (bacteria). Samples were taken from individual mussels at time 0 (control), at 2 (an additional time point to original proposal), 4, 8 and 24 hours. Samples were taken from gill, digestive gland, gonad/mantle, circulating haemocytes and muscle tissues and stored appropriately. RNA was extracted and in general (unless stated) equal volumes of RNA of each tissue type from each time point was pooled in order to generate the libraries, thereby all libraries contained equal representation of all tissues and all time points. In the case of the subtracted libraries the control and experimental RNA pools were sent separately. The libraries were created for both species from a variety of stress responses as follows:

*Mytilus galloprovincialis* Physical Stress SSH Library

Extracted RNA from pooled confirmed *Mytilus galloprovincialis* animals of haemocyte, gill, gonad/mantle, muscle and digestive gland and following a physical challenge experiment were taken. For control samples (time 0) a total of 8 μg was pooled equally from gill, gonad/mantle, muscle and digestive gland and 1 μg was pooled from haemocyte samples to make a total control sample of 9 μg RNA. For experimental pooling equal volumes (3 μg) were taken from haemocyte, gill, gonad/mantle, muscle and digestive glands from samples taken at 2 hours and 4 hours post-challenge (15 μg RNA total). As this is a subtracted library, a control pooled sample and test experimental pooled sample were used for library construction (Evrogen®). An aliquot of each pool (0.5 μg RNA) was used for ds cDNA synthesis and subtractive hybridization performed using SSH method in both directions. Two cDNA samples (40 ng each) enriched with differentially expressed sequences (control and test specific) were cloned into pAL16 vector and transformed into *E. coli*. Differential screening (duplicated nylon membranes and Virtual Northern Blot analysis) was used to confirm the presence of differential clones in control and experimental groups.

*Mytilus galloprovincialis* Environmental (Temperature, Hypoxia and Salinity) Stress Highly Normalized Library Equal amounts of RNA (2 μg) were taken from pooled confirmed *Mytilus galloprovincialis* animals of haemocyte, gill, gonad/mantle, muscle and digestive gland following hypoxia, temperature and salinity challenge experiments, taken from individuals at a control (time 0), 2, 4, 8 and 24 hour time period (a total of 30 μg). An aliquot of this pool (0.2 μg RNA) was used for ds cDNA synthesis and amplified cDNAs were normalized using Duplex-Specific thermostable nuclease (DSN) normalization. Normalized cDNAs were purified and ligated into pAL 17.3 vector and transformed into *E. coli*. Randomly selected clones were tested and contained all inserts, with no redundancy found, hence the library was considered highly normalized (Evrogen).

*Mytilus edulis* Environmental (Physical, Hypoxia and Salinity) Stress Highly Normalized Library Equal amounts of RNA (3 μg) were taken from pooled confirmed *Mytilus edulis* animals of haemocyte, gill, gonad/mantle, muscle and digestive gland following hypoxia, physical disturbance and salinity challenge experiments, taken from individuals at a control (time 0), 2, 4 and 24 hour time period (a total of 87 μg). An aliquot of this pool (0.2 μg RNA) was used for ds cDNA synthesis and amplified cDNAs were normalized using DSN normalization. Normalized cDNAs were purified and ligated into pAL 17.3 vector and transformed into *E. coli*. Randomly selected clones were tested and contained all inserts, with no redundancy found, hence the library was considered highly normalized (Evrogen).

*Mytilus edulis* Temperature Stress Highly Normalized Library

Equal amounts of RNA (3 μg) were taken from pooled confirmed *Mytilus edulis* animals of haemocyte, gill, gonad/mantle, muscle and digestive gland following temperature challenge experiments, taken from individuals at a control (time 0), 2, 4, 8 and 24 hour time period (a total of 75 μg). An aliquot of this pool (0.2 μg RNA) was used for ds cDNA synthesis and amplified cDNAs were normalized using DSN normalization. Normalized cDNAs were urified and ligated into pAL 17.3 vector and transformed into *E. coli*.

Randomly selected clones were tested and contained all inserts, with no redundancy found, hence the library was considered highly normalized (Evrogen).

*Mytilus edulis* Bacterial Stress SSH Library

Equal amounts of RNA (3 μg) were taken from pooled confirmed *Mytilus edulis* animals of haemocyte, gill, gonad/mantle, muscle and digestive gland following bacteria challenge experiments (inactivated *Vibrio tubiashii*), taken from individuals at a control (time 0 and 2 hours, total 30 μg RNA), 2, 4, 8 and 24 hour time period (total 60 μg RNA). As this is a subtracted library, a control pooled sample (18.42 μg) and test experimental pooled sample (22.43 μg RNA) were used for library construction (Evrogen). An aliquot of each pool (0.5 μg RNA) was used for ds cDNA synthesis and subtractive hybridization performed using SSH method in both directions. Four cDNA samples (40 ng each) enriched with differentially expressed sequences (control and test specific, as well as from Mirror orientation selection PCR (MOS PCR) were cloned into pAL16 vector and transformed into *E. coli*. Differential screening (duplicated nylon membranes and Virtual Northern Blot analysis) was used to confirm the presence of differential clones in control and experimental groups.

Example 2: Sequencing and Bioinformatics

Prior to sequencing a literature analysis was performed of known genome information of *Mytilus* species, in order to determine the most efficient method for generating useful sequence data. Data from National Center for Biotechnology Information (NCBI) databases and other specific mussel resources were pooled. A bi-directional sequencing strategy was employed, to maximize new gene discovery, which would also assist in comparisons to known genes. A total of 17,664 clones were sequenced, producing 35,327 Expressed Sequence Tags (ESTs) with an average length of 755 bp.

65% of the sequences were from the highly normalized libraries, and 35% from the SSH libraries (9% control, 26% experimental).

Sequences were compared to other *Mytilus* databases, to assist in generating functional assignments for each species. Bioinformatic analysis was performed and the final genes were selected for inclusion on the microarray. It was apparent that while there were some hits to terms for stress responses (e.g. cytochromes, heat shock proteins), there were also a large proportion of unknown or unclassified sequences.

Example 3: Microarray Design

A two species mussel oligonucleotide microarray (*Mytilus edulis* and *M. galloprovincialis*) was developed, using DNA sequences from the Myt-OME sequencing or from known literature sources. The subsequent array was designed using eArray®, the online Agilent® system, by Genotypic®. The array had a total of 15,088 features, of which 31% were probes relating to genes of known function from the Myt-OME database, 53% were probes relating to genes of unknown function (Myt-OME database), 12% were probes relating to genes of known stress function from other databases, and 4% were probes for control sequences. Sequence probes were either duplicated, triplicated or present as quads and the slide design incorporated eight replicated arrays per slide.

Example 4: Validation

The arrays were validated using *M. galloprovincialis* samples following physical stress with real-time quantitative Polymerase Chain Reaction (qPCR) assays.

Microarray experiments for *M. galloprovincialis* physical (gill and digestive gland only; time 0, 2 and 4 hours) and temperature stress (gill and digestive gland only; time 0, 2, 4, 8 and 24 hours), and *M. edulis* temperature stress (gill and digestive gland only; time 0, 2, 4, 8 and 24 hours) have been performed. Validations of the array expression show that there are highly significant correlations of microarray performance within (minimum r2=0.99) and between slides (minimum $r^2$=0.98), indicating high reproducibility of the arrays. ANOVA analysis showed that there was a significant influence of tissue, species and sample time on the gene expression profile produced. Significant differences were found between tissues, with gill expression profiles indicating more immediate and higher levels of gene expression fold changes than digestive gland samples. Digestive gland tissues showed closer correlation of gene expression with time, for both species, as opposed to the gill where higher individual variation was observed. Massive fold changes in gene expression were observed over time, but depending upon the tissue sampled the particular gene profiles varied. To date only microarray experimentation on individual samples has been conducted, rather than pooled samples, in order to examine potential individual variations in response.

Array validations were performed using real-time qPCR analysis and has shown relative levels of gene expression to the microarray (e.g. hsp70—FIG. 1), and differential responses over time (FIG. 2). Genes for both up-regulated and down-regulated responses were selected that are consistent across species and tissues and include genes of interest (hsps, sequestosome, apoptosis inhibitor and collectins) and reference genes (ATP5B, EF-1, GADPH, Histone H3 and 18S). Appropriate reference genes were chosen following reference gene analysis.

Example 5

*Mytilus* species from around the world, including, but not limited to *Mytilus edulis, Mytilus galloprovincialis* and *Mytilus trossulus* will be exposed to stresses, including, but not limited to metals, chemical toxins, microbes, hormones, pharmaceuticals, physical stress, thermal shock, hypoxia, wastewater and salinity. It will be determined that SEQ ID NO: 1-122 in combination will accurately demonstrate changes in gene expression of the genes from which the probes were ultimately designed. It will also be determined that subsets of SEQ ID NO: 1-122 will be effective in demonstrating changes in gene expression. It will also be determined that as few as 20 consecutive nucleotides or at least 30 consecutive nucleotides or at least 40 consecutive nucleotides, or 60 consecutive nucleotides of at least 50 or 80 or 122 sequences, and all ranges therebetween will be effective in demonstrating changes in gene expression. These changes in gene expression will be useful in monitoring the health of marine water. The microarray of the present technology was developed through a five stage process that highlights its features:
1. Stress libraries—five libraries for two *Mytilus* species and multiple tissues;
2. Sequencing—produced 17,664 clones;
3. Bioinformatics—35,327 Expressed Sequence Tags with an average read of 750 bases;
4. The microarray—8×15,000 oligoarray with 88% of the sequences from the MytOME database, of which 53% of the sequences are unknown genes involved in stress responses; and
5. Validation and repeatability—very strong correlations to real-time qPCR and with $r^2$ correlation coefficients >0.98 indicating the high repeatability and performance of the microarray.

Example 6

Gene expression patterns can be examined by using a microarray and also through a technique called reverse transcription real-time quantitative PCR (Q-RT-PCR). The Q-RT-PCR technique is based upon the traditional PCR technique, where an amplification process enables the identification of small amounts of nucleic acid (primarily DNA in this case). The amount of an expressed gene can be detected through measuring the amount of the mRNA transcript present within a sample, but it is necessary to amplify this gene transcript in order to robustly identify changes in gene expression in small amounts of RNA. In Q-RT-PCR the mRNA transcript is first reverse-transcribed to cDNA using reverse transcriptase, before commencing using real-time quantitative PCR to detect the levels of changes in gene expression using fluorophores. The rate at which the cDNA is amplified and detected is used to determine the relative gene expression of the original mRNA transcript.

We will use our probe sequences, and the genes they correspond to, indicated within this application to develop a real-time quantitative PCR assay for analysing gene expression. This assay may consist of single or multiple sets of probes and sequences listed herein, to examine the impact of changing ocean conditions on marine species.

Advantages of the exemplary embodiments described herein may be realized and attained by means of the instrumentalities and combinations particularly pointed out in this written description. It is to be understood that the foregoing general description and the following detailed description are exemplary and explanatory only and are not restrictive of the claims below. While example embodiments have been described in detail, the foregoing description is in all aspects illustrative and not restrictive. It is understood that numerous other modifications and variations can be devised without departing from the scope of the example embodiment.

While example embodiments have been described in connection with what is presently considered to be an example of a possible most practical and/or suitable embodiment, it is to be understood that the descriptions are not to be limited to the disclosed embodiments, but on the contrary, is intended to cover various modifications and equivalent arrangements included within the spirit and scope of the example embodiment. Those skilled in the art will recognize, or be able to ascertain using no more than routine experimentation, many equivalents to the specific example embodiments specifically described herein. Such equivalents are intended to be encompassed in the scope of the claims, if appended hereto or subsequently filed.

```
Sequence listing:
                                                        SEQ ID NO: 1
CCCATTGCTCAATGCCCAGGTTGTTTATAGGGCATTAATTGTGTAAATAACTAATAGATA

SEQ ID NO: 2
GGAAGTCACATCTTGTATGATTCTACTACAGATAATGTATCAAGTCCAGGAATGTATGTT

SEQ ID NO: 3
GTACCTGCATACTTTAATGATTCTCAAAGACTAGCCACAAAGGATGCTGGTTTCATTGCA

SEQ ID NO: 4
CATAATGAAGATGGTTCTAAAGGAATGAATCAAGACGACTCAAAAGGGTTCAATCAAGAC

SEQ ID NO:5
GACTCTTTCACTGTGGTAATAGTGGTTTTATGATGTCTTGGAGTTTAAACTGTTAAGAAC

SEQ ID NO: 6
GAGGTATGCACTTGGAAAATGAAAAATGCATCTGCGTGAAATTGCTCATACTATTTGCAA

SEQ ID NO: 7
GTACCATCGCGTAGGTTTCAAAGTCCTACTGATGAAATTACAAAAGTTAAAAGACTAGAA

SEQ ID NO: 8
TGATTCAAGGCAGAGCTAAAGGAGTTGAAGAGACAAAGGAGCGAGTCATTAATATTGAAC

SEQ ID NO: 9
CAAGTATTTTGAAAAGGGTATTCCAACCACTGGACACACTGAAATGTTAACATGATTGAA

SEQ ID NO: 10
ATAATGAAACTGGGAGGTCGGCTGATGTTCACCTTGATTTACTTAAACATTGAAACAAGC

SEQ ID NO: 11
GGATTAAAATGGGTGGTTGTTCCCAAAAAATCCCTCATTTCTTTTTTCTCCATGATTAAC

SEQ ID NO: 12
GTGAGTAGGGTCATTTTCGTGGAAACAGGTCTTCTTAATTTGATGACATAATGTATGTTA

SEQ ID NO: 13
CACCCACATATTAGTATTGGAAGAAAAAACCTGCCAAATATTGAGTTGATCTCTAATCCA

SEQ ID NO: 14
CGCATTTATAACATACATCATTCCACTCGAAGAAATAAACTTTCCCCCAATCTAGTCAAT

SEQ ID NO: 15
GAGGAGATCCCTTCCGAGATTTTGAGTAAAATGACAGTTTTAATTGAGTTCCAATTAACA

SEQ ID NO: 16
GCAATGCCAAAATAAGATGCGATTTTAATTATTGCAATGAACTTTCTTTCAGACCACTGC

SEQ ID NO: 17
CAGACAAGAGATTACTGGACTTTCCAGTTCCATTCAGTATTATTGATTCCGTCCAAGAAA

SEQ ID NO: 18
TGCAGAATGTGTAACCTAAAGGGAAGGATTCTAAAA CAGATCAAACGACATCTGGAGGAA

SEQ ID NO: 19
CTTGGGATTGTAACCTTTGGATTGGAAAGTGAAGATTGATCAAAGCAAAGGACTTAAATT

SEQ ID NO: 20
GCTATCTCTTTGATCTTCTGAGTGCTGTGATTAAGTAACATTTCCATGTATGCTTTACTT

SEQ ID NO: 21
AACGTCAGGACAAATACAAGCATTAAATCAATATACACATGTGAACGTCAGGACAAAACT

SEQ ID NO: 22
GCTAGTGTCGTTTGTGATAGTGAATGTCCTTGTGGAAATACAAAACGGCCTTGTATATGT
```

-continued

SEQ ID NO: 23
CAGGGATTCTTGGCATTATTTTCAGGTGACACTGGTGAAATTAAAAGTGAAGTAAGAGAA

SEQ ID NO: 24
GACGTCTGAAAAGCAGTAGACCTGTTTTTACTCGCATAATTTGCATCTTATGTAGAATT

SEQ ID NO: 25
CTTGTGTGATTTCATGTTACCAAGAACAATGATTAGTTGGTAGAGATAGCATCAGTAGAG

SEQ ID NO: 26
GCCTTATCGTCTGAATAATTAAATGGCGACTCTCAGCTGTAATTGTTGTTAAAATATGCA

SEQ ID NO: 27
CTCCGCCAGAGGCTGGCAAAAAGTTTTATATTGACAAAGGAAGCTCAAAATCAATAAAAT

SEQ ID NO: 28
GTGTATTGATAAAGCATGAAATGAGAGCAAAGAAAAATAGGGCGGCATTTACTTGTAACT

SEQ ID NO: 29
GTATGAACATCTGCTACAACAGATTCCATAACATATGAATCTTCAGACATTAAGAACGAC

SEQ ID NO: 30
CTGGTATCCAGCCTGTTTGTGGCAAATAAAACAAGGTTGTAAAAAAGATTATGGATTTGT

SEQ ID NO: 31
GGGCTATCGAAGAGATGGGGAAAACTCAAGATACGGATGAAAAGCACCATTAAAAGATAT

SEQ ID NO: 32
GCCTTAATGTTTCCTGGGTGATGCTTACACATTTGAATTGCAATTGTACCGTTCATGTAC

SEQ ID NO: 33
CCAAAAAGGAGGCAACTCAAATGTTAGGACAGATAATAGAATGTGTTAGGAATTTACCTA

SEQ ID NO: 34
TTATTGAATTATTTCTGTTGCCGTTACGTCTGTTTATCCACGAGTCTTTTAGGAATCTCT

SEQ ID NO: 35
GAAGCAGACAGATCTATTCATGATGCCCTGTGTGTTCTTACTCAGACAGTCAAGGAAACC

SEQ ID NO: 36
AGAGTTACATAACTTGGAAAAAAGAGTTGACTCAATGTTGTGATCTGATCTCAGGGATAA

SEQ ID NO: 37
GTGCAAAGTTATGACTGATTGTTTGCGATCAAATCGCTATCGTGGTGATAATAAATTGTG

SEQ ID NO: 38
CGACAGAACCAAGGATTTAATCAGTGTCCGCAGTTAAATTGAATATGTAGTCTTTGTTGC

SEQ ID NO: 39
GGTGTCAAAGATCACCAATATTCCACATTTTCTGTTTGACAGTAACCATCATAAATACAC

SEQ ID NO: 40
GCATTAGATTTGACAAATGAATTGTTAACATTAGTCCCAGGTCATGACAGGGCTTTAAAT

SEQ ID NO: 41
ACGTGATTGCCGATTGCGGTAAATTATTGCCTGTGAATTTATGATGTGAACATTTTAGAT

SEQ ID NO: 42
GTATCCTCATTTCTGTTGGTGATCGTTATTTTCGATTTTGTTGTTGACATGAGACAATCT

SEQ ID NO: 43
GGGCAGATTTAGAATATAAACCTCCTGTAGAAAAATCTTGACACAAGGATGACTAGTTTA

SEQ ID NO: 44
AGTGATTACACATTCAGTCAGAAATCCTTGTCAAGTTGTTATTGCCAGTTATACTTGCAT

SEQ ID NO: 45
ATGATGATTATGCTGGGTATCAAGACCATGACTTTGGAGGTGCTAGTGGGTTCTCCTTTG

SEQ ID NO: 46
AGAGCATTTAAAGAGAGAAATAAAATGGGTCGGTTTGCTGAAACAGATCCTGAAGAACTG

SEQ ID NO: 47
TAGGTCATGGACTTGGAGCCGGTGGTCATTTACCTGGCCTTAGTAAAGATATTGAAAAAA

SEQ ID NO: 48
GGATTTTGGCTTTTTTATTAGAATAGTTAGCATGTGCTGTAAAATCCCTATCAGATGTCC

SEQ ID NO: 49
GCAAAACCATGCCGATAGGTTGTGTAGAAAAATAAATTTTTGCTCAGTTTTGCTGATGAA

-continued

SEQ ID NO: 50
GACATCCAATATGATAAATATGTTGTACTTGTGTAAGACTCCAATAACCAGGGGAGATAA

SEQ ID NO: 51
ATTAAAGGCAGAAAAGTTAGAGCTTCTGAACCAGATGAAACAGTTGTACCTCGGCCGCGA

SEQ ID NO: 52
CCGGACGGGTTTGATTACGTTGCGGCTGGTGATATCCAAGCATTTTCATTATATAAAAAA

SEQ ID NO: 53
CTGTCATTGTTTTACATCACTTGCATGTGAGTATATGGTAATTAACTGAATAGGTTGGAG

SEQ ID NO: 54
GTAATTATGACCAATCATTTGTAATCCATCCTGGCAAAAGACTACCATGCTTTTATCTGA

SEQ ID NO: 55
CATATAATTTATTGATATAACTAAGAGTGTTATTGATCATGCATGAGGGTCTGGATGGGG

SEQ ID NO: 56
TGTATCATATGTGTGGATGAATGGAAGGAGTGCAAACAGAAATGGAAGGATCTCGAAAGA

SEQ ID NO: 57
AGGGGTTCTATCTCTGTACTTGTTGTTTTAGCAAAAGCAATATTGCATATCAAACACGAG

SEQ ID NO: 58
GTGGTAGACATATTGTTTGCAAAGTGAAGCTATGATACATCGAACATTTTATGTGTAGAG

SEQ ID NO: 59
CGACACTTTTCATTAACATCCATCCAACACATTGTGTATCCTGTTGAACTACATTTCATA

SEQ ID NO: 60
GACGGTATGCATCATGCAACTATTGGTTCGCAAACACATTTTACACATATTCTTTTTATC

SEQ ID NO: 61
AGGAGTAAACATCCATAGATCTGAGTTTTGAGATCAAACGAGGAAGCCTAAGAAATTTTA

SEQ ID NO: 62
TTATTGAATTATTTCTGTTGCCGTTACGTCTGTTTATCCACGAGTCTTTTAGGAATCTCT

SEQ ID NO: 63
ATGTGTTGGCATTAACATTGACCATATGTGTTGGCATTAACATTGACCATATGTGTTGGC

SEQ ID NO: 64
TGGACCAGGCTGGCTAAATATGGTTTTCATGGCTTTGGCATTTGTTTTCAGCTGAAAGAC

SEQ ID NO: 65
CGGGTAAAGCTGTAAATCCACAAGTCTTTCAGAATAAGTAGGTTGTATGAAGAATTGTTA

SEQ ID NO: 66
GAATAAAATTCTTTGGCTTCTTCGATTGATCTCAAAACTCAGATCTATGGATGTTTGCCC

SEQ ID NO: 67
GGTTACTTTGAAGTAAATTGAGAACATGTTACCTATTTGTTTGTTGTTGGTTGGACACCT

SEQ ID NO: 68
CATTACGGCCGGGGCAGACAAAACATATGGTTAGATATCAATTGAACATTTAAAATTTCA

SEQ ID NO: 69
TTTAGGAGCTATCTTGAACTTTAGTGTTGTGTGAGCTTTGTTCTTTCAAAGGCTTCACTG

SEQ ID NO: 70
AACAAGAACCGGGAATGTGGTATCAGCTCTCTAAAGATGAAATTGTTGATAAACAACTTA

SEQ ID NO: 71
GGGGCCAAAGGTCATGTGGATTTGACAACAGAATCGGAAGAGGATTTATTAATAGTATAG

SEQ ID NO: 72
ATAACAACACCTAGTCAAGGACTCTTTGGAGCTTTTGGAGGTCCATCTTTTGGAGGAGGA

SEQ ID NO: 73
AGCGAGGTTATCATTATTCTTGACACTTGACCACTCACATATTAAACCTGCATCTAATTT

SEQ ID NO: 74
AGAGAAGTTTATTGAGGCTGTTCAACAAGGGGAAAATCCAGAGATAACTAAAAATGTGGC

SEQ ID NO: 75
TCTGAACTTACTGTCTCAATTGCTACGTGAAATTTTTGTTGCAACAGTTATCGTGATAGC

SEQ ID NO: 76
CTGGAACCAGTTGAAAAAGCTTTAAGAGACGCTAAACTTGATAAAAGTAGTATTCAAGAG

-continued

SEQ ID NO: 77
GTGCAATATTATAACTGTTGAATGGTATTTCATTTCCTTGCAGCTTGTGTGAAGCAAACA

SEQ ID NO: 78
CTGAAGTCCTTGTTGGTACATTAAAACCGGCATCTTGGTCGATTTCTTTCACAGAAAAAA

SEQ ID NO: 79
TATGGCAGAGAAAGACAAAGCTAGATATGAGGGAGAAAATGCAAATTACGAGCCAGGACC

SEQ ID NO: 80
GTGTAACTTTAGTAGAGGAAAGGTTAGTGGACAAATAGTGGATTACCTCATATGAATGAA

SEQ ID NO: 81
TCGACAACAAACCAACCAAACTTCAGATGCTGACTCTCAGAAGAATAAAGGAGGAAAAAA

SEQ ID NO: 82
ACTATGACAATGACAGAGTTCGTGACTGTTTATATCTGAAATAAATCAGCAGATGTCTCC

SEQ ID NO: 83
CATTCCTTGGATTAATAGCATCGTTGGACAGTAAACAGTTAAATGTGCTTGTTTAACATG

SEQ ID NO: 84
GACGTCTGAAAAGCAGTAGACCTGTTTTTTACTCGCATAATTGCATCTTATGTAGAATTT

SEQ ID NO: 85
GCAGGAGCAACAACAAAAGTATCTCTAAATCAAGATCAAGATCTCCTGAGTAAAATAACA

SEQ ID NO: 86
TAGAGATGGTCGAGCATCACTTTTCTTTGGATAAATCGCATGAAACAGTTGCACTACTTT

SEQ ID NO: 87
GTCTGTTTACAGTGCTGAATCAATAATTGCTCTTGGAACACCCAAAATTAAAAGTGCAAA

SEQ ID NO: 88
CGGGAATAGTGCAATTTGTTTCGTGTGTGATAAACACAGTACAAAATAGAATTGTTTGCA

SEQ ID NO: 89
GTGAACGTCCAATGACCAAAGACAACCATCAACTTGGTAAATTCGACCTGACTGGCATTC

SEQ ID NO: 90
CAGTTGTGTTTGCATGTTCATGGCTATCCTAGTTATAGAAATAAAAGGAATATCAAGTCC

SEQ ID NO: 91
GAATCAAGACACATCCCTATGCAATCAAAGAAAACAAACTGGGTTTGTTGTGTACATAAT

SEQ ID NO: 92
TAGGGACTTTGCGGAATGTGTTGTGATATTCGTATGATTAACAACACTGTAGTGTTATAA

SEQ ID NO: 93
CAATGGGAGATTACTCTAGAAGTACAAATAGAATGTATTGGTGACCGTGATCATATTACA

SEQ ID NO: 94
CCTACCTTCCCACATTCATCTTTCTGGGATAGTCCTGAATATTACTTCCATGCATATATT

SEQ ID NO: 95
TGGGGGATGGCCCAGTTGCTTTGATGAAGCTAAGCTCAAAAGTAGTTTATTGCTCTGAGT

SEQ ID NO: 96
GGGTTTACTATGTTCGTTGTCATCTCATCATTGCATTACCTGTGATCAAGAAAAACTATA

SEQ ID NO: 97
GCATATATCCATTGTGCTCTTACAGTAATTGTTAACATTAGACATCGTTTGCTACATGTG

SEQ ID NO: 98
CTCTGACACATTGATGCATTCAAACTTCATGCTTGGTGTCATACCAGTCTTATAAATTAT

SEQ ID NO: 99
CTGACAATGACACAATGACAGCATATTTTGCATTTTCAGTACAGATGGGTATGTTGTATA

SEQ ID NO: 100
GCATTGCTGATTCGGTTTCTCGAAAACTGTGTAACATTTCAATACTGACAATCATTATTC

SEQ ID NO: 101
TTGGCTTCCAACATGTCTGTGCAGAATTCATACGTTATTACAGAACATGATGTTATACAT

SEQ ID NO: 102
CGAGCTTATGATATCATGACCATGCTGTATCTTTTTCATACCATTTGTACCTCGGCCGCG

SEQ ID NO: 103
ATTGAAGTCTGTCAGCAGACCAAAAATAATATGCTTGCTGTAATGGAAATAACTTACTGC

-continued

SEQ ID NO: 104
ATCAGTTGATCATCAGAGAATCACATTCAGAAGCTCGTGAAGCTAATCAAGCTACACAAA

SEQ ID NO: 105
GTGTGGAGCCAATTCAAGAGATAGGGTTGGAAAGATTTATAAAATCCAAATTGCTGGAAT

SEQ ID NO: 106
ATGTTGACATGTCATCTGATGATTCTGATGAAGAAACACCTCAAACCACCAAGTCTGGTA

SEQ ID NO: 107
AATAAAGTTTGACAACAGCTAAATCCTATACTCCAACTCAGACCCCACCACACTGTGTT

SEQ ID NO: 108
TCTCATAGTTTAACAAGAAGCGGTTATAATCTGATCGTTACTGTAAAAAATAGTCCGGAG

SEQ ID NO: 109
CGGTGTCATGTGCGTCTGTTACTTTTGATATTTCAGATACTCGTGTAATGCGTACCTCGG

SEQ ID NO: 110
CCCATTTTTATAAACTGCTTTATTTTCAAGTGTAAACTGTCTTTATGTACCTCGGCCGCG

SEQ ID NO: 111
GAATATTCATTGTGTGACACAGAGGTCACTCTAAAAATGTCTCACTGTTTTCTTACTCAT

SEQ ID NO: 112
CGAACAAGTGACATATGCAGTTACTATTGCGTAATAGTCCAGACATTTATAGAACATTAG

SEQ ID NO: 113
GCAGCTTAGTAAGGTGTGTCTAATTTATTTGGGAGAAATCCTTTGTGTTTGTTTGTAATG

SEQ ID NO: 114
CGAGAAATTGAAAGGAAATTCATGTTGACCTTTCAAAATGGACACACTTCAGGAAATCAT

SEQ ID NO: 115
CTAAAAACAGAGGAAGCCAATACTTTAAGAAAGAAAACTACAGCAAGGCAAAGCAGTTCT

SEQ ID NO: 116
CTTGTTTGAAAGCCGTCAGTTTGTCGAACTTCTGCATGCTACTTTTGGTGCAAAGGTTGA

SEQ ID NO: 117
AACGCAAATTTATCCAAGATGTGGGCCTGGGGATTCGTTATATTACAATAATTCTTGTTA

SEQ ID NO: 118
GAAGCGGTTAAACGCATGTGTGTTCATTTATGACAATTAAGAAATTTATCGAAAGTGGTG

SEQ ID NO: 119
GGCTTCACATGCCTTTGAACAATCAAAAACATGGAATCGTATGGCAATTGGTTAATTATT

SEQ ID NO: 120
GGAGACATAAAATCTACACCAGTAACCACATTATGCAAGGGATACATTACATTCTGCTGA

SEQ ID NO: 121
GTGAATATATCAGATCTTCGAGGCACACGTGATTAGACTTAAGTTCATATTCGTGATATA

SEQ ID NO: 122
CATGACCCGCAATAGTGTCGCAAACGAAAGTAAGTTACATTTAAAAGAATGGAGGAAGAA

The invention claimed is:

1. A kit for monitoring environmental quality of marine water, the kit comprising a suitably selected buffer, and a plurality of probes immobilized on a substrate to provide a microarray, the microarray having a set of probes that individually comprise at least 20 consecutive nucleotides of at least SEQ ID NO: 1, 3-10, 16 and 30.

2. The kit of claim 1, wherein the set of probes individually comprise at least 40 consecutive nucleotides of at least SEQ ID NO: 1, 3-10, 16 and 30.

3. The kit of claim 2 comprising at least 80 probes in the microarray.

4. The kit of claim 2, wherein the set of probes individually comprise 60 consecutive nucleotides of at least SEQ ID NO: 1, 3-10, 16 and 30.

5. The kit of claim 1, wherein the probes within the set of probes individually consist of between 20 and 60 nucleotides in total length.

* * * * *